(12) United States Patent
Dassau et al.

(10) Patent No.: US 12,161,463 B2
(45) Date of Patent: Dec. 10, 2024

(54) PREVENTION OF POST-BARIATRIC HYPOGLYCEMIA USING A NOVEL GLUCOSE PREDICTION ALGORITHM AND MINI-DOSE STABLE GLUCAGON

(71) Applicants: PRESIDENT AND FELLOWS OF HARVARD COLLEGE, Cambridge, MA (US); JOSLIN DIABETES CENTER, INC., Boston, MA (US)

(72) Inventors: Eyal Dassau, Acton, MA (US); Alejandro J. Laguna Sanz, Cambridge, MA (US); Mary-Elizabeth Rueckel Patti, Newton, MA (US); Francis J. Doyle, III, Chestnut Hill, MA (US)

(73) Assignees: PRESIDENT AND FELLOWS OF HARVARD COLLEGE, Cambridge, MA (US); JOSLIN DIABETES CENTER, INC., Boston, MA (US)

( * ) Notice: Subject to any disclaimer, the term of this patent is extended or adjusted under 35 U.S.C. 154(b) by 121 days.

(21) Appl. No.: 16/003,338

(22) Filed: Jun. 8, 2018

(65) Prior Publication Data
US 2018/0353112 A1   Dec. 13, 2018

Related U.S. Application Data

(60) Provisional application No. 62/517,627, filed on Jun. 9, 2017.

(51) Int. Cl.
*A61B 5/145*   (2006.01)
*A61B 5/00*    (2006.01)
(Continued)

(52) U.S. Cl.
CPC ........ *A61B 5/14532* (2013.01); *A61B 5/7275* (2013.01); *A61B 5/746* (2013.01);
(Continued)

(58) Field of Classification Search
CPC ... A61B 5/14532; A61B 5/7275; A61B 5/746; A61B 5/0031; A61B 5/14503;
(Continued)

(56) References Cited

U.S. PATENT DOCUMENTS 5,707,641 A  *  1/1998  Gertner ............... A61K 9/0014
                                              424/484
5,746,697 A     5/1998  Swedlow et al.
(Continued)

FOREIGN PATENT DOCUMENTS

WO      2018/009614 A1    1/2018

OTHER PUBLICATIONS

Colleen M. Craig, et al., "Critical role for GLP-1 in symptomatic post-bariatric hypoglycaemia", Diabetologia (2017) 60:531-540, DOI 10.1007/s00125-016-4179-x.
(Continued)

*Primary Examiner* — Alex M Valvis
*Assistant Examiner* — Justin Xu
(74) *Attorney, Agent, or Firm* — Nixon Peabody LLP; David S. Resnick; Wayne Tang

(57) ABSTRACT

The present disclosure provides a hypoglycemia prediction algorithm (HPA) specifically designed for the unique postprandial glycemic patterns characteristic of PBH. This algorithm can predict impending hypoglycemia by performing a series of steps. The steps can include collecting data from at least one sensor. The data can comprise a concentration of glucose in the bloodstream of a subject. The data can be processed using the HPA and impending glucose concentrations can be calculated. The method can then provide for determining whether the predicted glucose concentrations are lower than a hypoglycemic threshold parameter. In response to determining that the predicted glucose concentrations are lower than the hypoglycemic threshold param-
(Continued)

eter, the method can provide for enacting an impending hypoglycemia protocol.

10 Claims, 19 Drawing Sheets

(51) Int. Cl.
  *A61K 38/26* (2006.01)
  *A61M 5/172* (2006.01)
  *G16H 50/30* (2018.01)
(52) U.S. Cl.
  CPC ............ *A61K 38/26* (2013.01); *A61B 5/0031* (2013.01); *A61B 5/14503* (2013.01); *A61B 5/4839* (2013.01); *A61B 5/7203* (2013.01); *A61B 5/7282* (2013.01); *A61M 5/1723* (2013.01); *A61M 2205/35* (2013.01); *A61M 2205/50* (2013.01); *A61M 2230/201* (2013.01)
(58) Field of Classification Search
  CPC ... A61B 5/7282; A61B 5/4839; A61B 5/7203; A61K 38/26; A61M 2205/35; A61M 2230/201; A61M 2205/50; A61M 5/1723; G16H 50/30
  See application file for complete search history.

(56) References Cited

U.S. PATENT DOCUMENTS

| | | | |
|---|---|---|---|
| 10,117,992 B2* | 11/2018 | Parikh | A61M 5/14244 |
| 10,546,659 B2 | 1/2020 | Kovatchev et al. | |
| 2004/0122353 A1 | 6/2004 | Shahmirian et al. | |
| 2004/0158232 A1 | 8/2004 | Schetky et al. | |
| 2005/0044436 A1 | 2/2005 | Holle | |
| 2005/0272640 A1 | 12/2005 | Doyle et al. | |
| 2007/0016127 A1 | 1/2007 | Staib et al. | |
| 2007/0244575 A1 | 10/2007 | Wojsznis et al. | |
| 2007/0276512 A1 | 11/2007 | Fan et al. | |
| 2008/0033271 A1* | 2/2008 | Say | A61B 5/14865 600/347 |
| 2008/0208113 A1 | 8/2008 | Damiano et al. | |
| 2008/0235053 A1* | 9/2008 | Ray | G16H 50/20 600/300 |
| 2009/0143725 A1* | 6/2009 | Peyser | A61B 5/14546 600/365 |
| 2009/0315772 A1 | 12/2009 | Wengler et al. | |
| 2010/0198142 A1* | 8/2010 | Sloan | G16H 20/10 345/173 |
| 2010/0262117 A1 | 10/2010 | Magni et al. | |
| 2010/0280441 A1 | 11/2010 | Wilinska et al. | |
| 2010/0298685 A1 | 11/2010 | Hayter et al. | |
| 2011/0098548 A1 | 4/2011 | Budiman et al. | |
| 2011/0106011 A1 | 5/2011 | Cinar et al. | |
| 2011/0208156 A1 | 8/2011 | Doyle et al. | |
| 2013/0018232 A1 | 1/2013 | D'Souza et al. | |
| 2014/0005633 A1 | 1/2014 | Finan | |
| 2014/0081236 A1 | 3/2014 | Wilinska et al. | |
| 2014/0121488 A1 | 5/2014 | Budiman | |
| 2014/0180240 A1 | 6/2014 | Finan et al. | |
| 2014/0200559 A1 | 7/2014 | Doyle et al. | |
| 2014/0276554 A1 | 9/2014 | Finan et al. | |
| 2014/0276555 A1 | 9/2014 | Morales | |
| 2014/0379273 A1* | 12/2014 | Petisce | G16H 15/00 702/19 |
| 2015/0100038 A1 | 4/2015 | Mccann et al. | |
| 2015/0134356 A1 | 5/2015 | Atlas et al. | |
| 2015/0309486 A1 | 10/2015 | Webersinke et al. | |
| 2016/0030670 A1* | 2/2016 | Fischl | A61M 5/1723 604/504 |
| 2016/0038673 A1 | 2/2016 | Morales | |
| 2016/0048119 A1 | 2/2016 | Wojsznis et al. | |
| 2016/0163037 A1 | 6/2016 | Dehais et al. | |
| 2016/0170384 A1 | 6/2016 | Charest-Finn et al. | |
| 2016/0281489 A1 | 9/2016 | Dykstra et al. | |
| 2017/0000943 A1 | 1/2017 | Blomquist et al. | |
| 2017/0017212 A1 | 1/2017 | Collins et al. | |
| 2017/0099011 A1 | 4/2017 | Freeman et al. | |
| 2017/0136160 A1 | 5/2017 | Barral et al. | |
| 2017/0143899 A1 | 5/2017 | Gondhalekar et al. | |
| 2017/0173262 A1 | 6/2017 | Veltz | |
| 2017/0192400 A1 | 7/2017 | Hofschulz et al. | |
| 2017/0216518 A1 | 8/2017 | Davis et al. | |
| 2017/0249445 A1 | 8/2017 | Devries et al. | |
| 2018/0147349 A1 | 5/2018 | Finan et al. | |
| 2018/0271418 A1* | 9/2018 | Hayter | G16H 50/20 |
| 2018/0369479 A1 | 12/2018 | Hayter et al. | |
| 2019/0244713 A1* | 8/2019 | Van Orden | G16H 50/30 |
| 2020/0268968 A1* | 8/2020 | Steil | A61M 5/172 |

OTHER PUBLICATIONS

Eyal Dassau et al., "Adjustment of Open-Loop Settings to Imporove Closed-Loop Results in Type 1 Diabetes: A Multicenter Randomized Trial", J Clin Endocrinol Metab. Oct. 2015; 100(10): 3878-3886, Published online Jul. 23, 2015, pp. 1-14.

Florencia Halperin et al., "Continuous Glucose Monitoring for Evaluation of Glycemic Excurisions after Gastric Bypass", Hindawi Publishing Corporation, Journal of Obesity, vol. 2011, Article ID 869536, 7 pages.

Florencia Halperin et al., "Glucagon Treatment for Post-Gastric Bypass Hypoglycemia", Short Communications, Integrative Physiology, vol. 18, No. 9, Sep. 2010, pp. 1858-1860.

Rebecca A. Harvey, B.S., et al., "Design of the Health Monitoring System for the Artificial Pancreas: Low Glucose Prediction Module", Journal of Diabetes Science and Technology, vol. 6, Issue 6, Nov. 2012, pp. 1345-1354.

Rebecca A. Harvey, Phd., et al., "Clinical Evaluation of an Automated Artificial Pancreas Using Zone-Model Predictive Control and Health Monitoring System", Diabetes Technology & Therapeutics, vol. 16, No. 6, 2014, pp. 348-357.

Morey W. Haymond, et al., "Nonaqueaus, Mini-Dose Glucagon for Treatment of Mild Hypoglycemia in Adults With Type 1 Diabetes: A Dose-Seeking Study", Diabetes Care, vol. 39, Mar. 2016, pp. 465-468.

Emmy Suhl et al., "Medical Nutrition Therapy for Post-Bariatric Hypoglycemia: Practical Insights", Surg Obes Relat Dis., May 2017, 13(5), 888-896, doi: 10.1016/j, soard, 2017, 01, 025.

Gondhalekar et al. "MPC Design for Rapid Pump-Attenuation and Expedited Hyperglycemia Response to Treat T1DM with an Artificial Pancreas." Proc Am Control Conf 4224-4230 (2014).

Gondhalekar et al. "Velocity-weighting & velocity-penalty MPC of an artificial pancreas: Improved safety & performance." Automatica 91: 105-117 (2018).

Shi et al. "Adaptive Zone Model Predictive Control of Artificial Pancreas Based on Glucose-and Velocity-Dependent Control Penalties." IEEE Transactions on Biomedical Engineering 66(4): 1045-1054 (2019).

Forlenza et al. "Application of zone model predictive control artificial pancreas during extended use of infusion set and sensor: a randomized crossover-controlled home-use trial." Diabetes Care 40(8): 1096-1102 (2017).

Liu et al. "Insulin is a stronger inducer of insulin resistance than hyperglycemia in mice with type 1 diabetes mellitus (T1DM)." Journal of Biological Chemistry 284(40): 27090-27100 (2009).

Fougner et al. "Intraperitoneal glucose sensing is sometimes surprisingly rapid." Modeling, Identification and Control 37(2): 121-131 (2016).

Fritsch et al. "Monotone piecewise cubic interpolation: algorithms and software." Siam J. Numer. Anal. 17(2): 238-246 (1980).

Garg et al. "Glucose outcomes with the in-home use of a hybrid closed-loop insulin delivery system in adolescents and adults with type 1 diabetes." Diabetes technology & therapeutics 19(3): 155-163 (2017).

"Gillis et al. ""Glucose estimation and prediction through meal responses using ambulatory subject data for advisory mode model predictive control."" Journal of Diabetes Science and Technology1(6): 825-833 (2007)".

(56) References Cited

OTHER PUBLICATIONS

Gin et al. "Combined improvements in implantable pump technology and insulin stability allow safe and effective long term intraperitoneal insulin delivery in type 1 diabetic patients: the EVADIAC experience." Diabetes & metabolism 29(6): 602-607 (2003).
Goldfine et al. "Patients with neuroglycopenia after gastric bypass surgery have exaggerated incretin and insulin secretory responses to a mixed meal." The Journal of Clinical Endocrinology & Metabolism 92(12): 4678-4685 (2007).
Goldfine et al. "How common is hypoglycemia after gastric bypass ?." Obesity (Silver Spring, Md.) 24(6): 1210-11 (2016).
Gondhalekar et al. "Periodic-zone model predictive control for diurnal closed-loop operation of an artificial pancreas." Journal of Diabetes Science and Technology 7(6): 1446-1460 (2013).
Gondhalekar et al. "Moving-horizon-like state estimation via continuous glucose monitor feedback in MPC of an artificial pancreas for type 1 diabetes." 53rd IEEE Conference on Decision and Control. IEEE. 310-315 (2014).
Gondhalekar et al. "Tackling problem nonlinearities & delays via asymmetric, state-dependent objective costs in MPC of an artificial pancreas." IFAC—PapersOnLine 48(23): 154-159 (2015).
Gondhalekar et al. "Velocity-weighting to prevent controller-induced hypoglycemia in MPC of an artificial pancreas to treat T1DM." 2015 American Control Conference (ACC). IEEE. 1635-1640 (2015).
Gondhalekar et al. "Periodic zone-MPC with asymmetric costs for outpatient-ready safety of an artificial pancreas to treat type 1 diabetes." Automatica 71: 237-246 (2016).
Gonzales et al., "Model predictive control tuning based on Extended Kalman Filter." 2017 IEEE Second Ecuador Technical Chapters Meeting (ETCM). IEEE, (2017).
Gonzalez et al., "A stable MPC with zone control", Journal of Process Control 19(1):110-122 (2009).
Gonzalez-Gonzalez et al. "Use of diazoxide in management of severe postprandial hypoglycemia in patient after Roux-en-Y gastric bypass." Surgery for Obesity and Related Diseases 9(1): e18-e19 (2013).
Goodyear et al. "Exercise, glucose transport, and insulin sensitivity." Annual review of medicine 49(1): 235-261 (1998).
Gregory et al. "Insulin delivery into the peripheral circulation: a key contributor to hypoglycemia in type 1 diabetes." Diabetes 64(10): 3439-3451 (2015).
Grosman et al., "Zone model predictive control: a strategy to minimize hyper-and hypoglycemic events" Journal of diabetes science and technology 4(4): 961-975 (2010).
Grosman et al. "Multi-zone-MPC: Clinical inspired control algorithm for the artificial pancreas." IFAC Proceedings vols. 44(A1161): 7120-7125 (2011).
Grosman et al. "Hybrid closed-loop insulin delivery in type 1 diabetes during supervised outpatient conditions." Journal of diabetes science and technology 10(3): 708-713 (2016).
Haidar. "The artificial pancreas: How closed-loop control is revolutionizing diabetes." IEEE Control Systems Magazine 36(5): 28-47 (2016).
Halperin et al. "Roux-en-Y gastric bypass surgery or lifestyle with intensive medical management in patients with type 2 diabetes: feasibility and 1-year results of a randomized clinical trial." JAMA surgery 149(7): 716-726 (2014).
Heemels et al. "An introduction to event-triggered and self-triggered control." 2012 IEEE 51st IEEE conference on decision and control (CDC). IEEE.1-16 (2012).
Heise et al. "Insulin stacking versus therapeutic accumulation: understanding the differences." Endocrine Practice 20(1): 75-83 (2014).
Hepburn et al. "Symptoms of acute insulin-induced hypoglycemia in humans with and without IDDM: factor-analysis approach." Diabetes Care 14(11): 949-957 (1991).
Horton. "Exercise and physical training: effects on insulin sensitivity and glucose metabolism." Diabetes/metabolism reviews 2(1-2): 1-17 (1986).
Horwitz et al. "Proinsulin, insulin, and C-peptide concentrations in human portal and peripheral blood." The Journal of clinical investigation 55(6): 1278-1283 (1975).
Hovorka et al. "Nonlinear model predictive control of glucose concentration in subjects with type 1 diabetes." Physiological measurement 25(4): 905-920 (2004).
Hovorka. "Continuous glucose monitoring and closed-loop systems." Diabetic medicine 23(1): 1-12 (2006).
Hu et al., "An improved PID algorithm based on insulin-on-board estimate for blood glucose control with Type 1 diabetes." Computational and Mathematical Methods in Medicine 2015(281589):1-9 (2015).
Huyett et al. "Design and evaluation of a robust PID controller for a fully implantable artificial pancreas." Industrial & engineering chemistry research 54(42): 10311-10321 (2015).
Huyett et al. "Preliminary evaluation of a long-term intraperitoneal glucose sensor with flushing mechanism." Journal of diabetes science and technology 10(5): 1192-1194 (2016).
Huyett et al. "Outpatient closed-loop control with unannounced moderate exercise in adolescents using zone model predictive control." Diabetes technology & therapeutics 19(6): 331-339 (2017).
Jost et al. "Optimal and suboptimal event-triggering in linear model predictive control." 2015 European Control Conference (ECC). IEEE 14: 1147-1152 (2015).
Kellogg et al. "Postgastric bypass hyperinsulinemic hypoglycemia syndrome: characterization and response to a modified diet." Surgery for Obesity and Related Diseases 4(4): 492-499 (2008).
Kerfurt et al. "Hypoglycemia after Roux-En-Y gastric bypass: detection rates of continuous glucose monitoring (CGM) versus mixed meal test." Surgery for Obesity and Related Diseases 11(3): 564-569 (2015).
Kirchsteiger et al. "Robustness properties of optimal insulin bolus administrations for type 1 diabetes." American Control Conference. IEEE: 2284-2289 (2009).
Knab et al. "Zone model predictive control and moving horizon estimation for the regulation of blood glucose in critical care patients." IFAC—PapersOnLine 48(8): 1002-1007 (2015).
Koerker et al. "Somatostatin: hypothalamic inhibitor of the endocrine pancreas." Science 184(4135): 482-484 (1974).
Kovatchev et al. "In silico preclinical trials: a proof of concept in closed-loop control of type 1 diabetes."Journal of Diabetes Science and Technology3(1): 44-55 (2009).
Kovatchev et al. "Safety of outpatient closed-loop control: first randomized crossover trials of a wearable artificial pancreas." Diabetes care 37(7): 1789-1796 (2014).
Kovatchev et al. "Feasibility of long-term closed-loop control: a multicenter 6-month trial of 24/7 automated insulin delivery." Diabetes technology & therapeutics 19(1): 18-24 (2017).
Lee et al., "A Closed-loop Artificial Pancreas based on the MPC: human friendly identification and automatic meal disturbance rejection." IFAC Proceedings 41(2): 4252-4257 (2008).
Lee et al. "Design and in silico evaluation of an intraperitoneal-subcutaneous (IP-SC) artificial pancreas." Computers & chemical engineering 70: 180-188 (2014).
Lee et al., "Enhanced model predictive control (eMPC) strategy for automated glucose control." Industrial & engineering chemistry research 55(46): 11857-11868 (2016).
Lehmann et al. "Event-triggered model predictive control of discrete-time linear systems subject to disturbances." 2013 European Control Conference (ECC). IEEE:1-6 (2013).
Liebl et al. "A reduction in severe hypoglycaemia in type 1 diabetes in a randomized crossover study of continuous intraperitoneal compared with subcutaneous insulin infusion." Diabetes, obesity and metabolism 11(11): 1001-1008 (2009).
Abrahamsson et al. "Gastric bypass reduces symptoms and hormonal responses in hypoglycemia." Diabetes 65(9): 2667-2675 (2016).
Andersen et al. "Interior-point methods for large-scale cone programming." Optimization for machine learning 5583: 56-83 (2011).
Banerjee et al. "Model based safety analysis and verification of cyber-physical systems" Dissertation, Arizona State University (2012).

(56) References Cited

OTHER PUBLICATIONS

Bansal et al. "Goal-driven dynamics learning via Bayesian optimization." 2017 IEEE 56th Annual Conference on Decision and Control (CDC). IEEE, 5168-5173 (2017).
Bell et al. "Impact of fat, protein, and glycemic index on postprandial glucose control in type 1 diabetes: implications for intensive diabetes management in the continuous glucose monitoring era." Diabetes care 38(6): 1008-1015 (2015).
Bemporad et al. "The explicit linear quadratic regulator for constrained systems." Automatica 38(1): 3-20 (2002).
Benosman et al. "Bayesian optimization-based modular indirect adaptive control for a class of nonlinear systems." IFAC—PapersOnLine 49(13): 253-258 (2016).
Bergenstal et al. "Safety of a hybrid closed-loop insulin delivery system in patients with type 1 diabetes." Jama 316(13): 1407-1408 (2016).
Bernardini et al. "Energy-aware robust model predictive control based on noisy wireless sensors." Automatica 48(1): 36-44 (2012).
Blauw et al. "Performance and safety of an integrated bihormonal artificial pancreas for fully automated glucose control at home." Diabetes, Obesity and Metabolism 18(7): 671-677 (2016).
Breton et al. "Fully integrated artificial pancreas in type 1 diabetes: modular closed-loop glucose control maintains near normoglycemia." Diabetes 61(9): 2230-2237 (2012).
Bristow et al. "A survey of iterative learning control." IEEE control systems magazine 26(3): 96-114 (2006).
Burnett et al. "Glucose sensing in the peritoneal space offers faster kinetics than sensing in the subcutaneous space." Diabetes 63(7): 2498-2505 (2014).
Cameron et al., "A closed-loop artificial pancreas based on risk management." Journal of diabetes science and technology 5(2): 368-379 (2011).
Cameron et al. "Extended multiple model prediction with application to blood glucose regulation," J. Process Control 22(8): 1422-1432 (2012).
Campos-Cornjeo et al. "An advisory protocol for rapid-and slow-acting insulin therapy based on a run-to-run methodology." Diabetes Technology & Therapeutics 12.7 (2010): 555-565.
Campos-Cornejo et al. "Adaptive control algorithm for a rapid and slow acting insulin therapy following run-to-run methodology." Proceedings of the 2010 American Control Conference. IEEE (2010).
Campos-Delgado et al. "Self-tuning insulin adjustment algorithm for type 1 diabetic patients based on multi-doses regime." Applied Bionics and Biomechanics 2(2): 61-71 (2005).
Campos-Delgado et al. "Fuzzy-based controller for glucose regulation in type-1 diabetic patients by subcutaneous route." IEEE Transactions on Biomedical Engineering 53(11): 2201-2210 (2006).
Castle et al. "Comparative pharmacokinetic/pharmacodynamic study of liquid stable glucagon versus lyophilized glucagon in type 1 diabetes subjects." Journal of diabetes science and technology 10(5): 1101-1107 (2016).
Ceriello et al. "Postprandial glucose regulation and diabetic complications." Archives of internal medicine 164(19): 2090-2095 (2004).
Cescon et al. "Impulsive predictive control of T1DM glycemia: an in-silico study." Dynamic Systems and Control Conference. American Society of Mechanical Engineers vol. (45295): 319-326 (2012).
Chakrabarty et al. "Support vector machine informed explicit nonlinear model predictive control using low-discrepancy sequences." IEEE Transactions on Automatic Control 62(1): 135-148 (2016).
Chakrabarty et al. "Event-triggered model predictive control for embedded artificial pancreas systems." IEEE Transactions on Biomedical Engineering 65(3): 575-586 (2017).
Charest et al., "MPC enhancement for tracking of complex profiles—The basic technique." Control Engineering Practice 33: 136-147 (2014).
Cherrington et al. "The role of insulin and glucagon in the regulation of basal glucose production in the postabsorptive dog." The Journal of clinical investigation 58(6): 1407-1418 (1976).

Cherrington. "Control of glucose uptake and release by the liver in vivo." Diabetes 48(5): 1198-1214 (1999).
Clark et al. "Even silent hypoglycemia induces cardiac arrhythmias." Diabetes 63(5): 1457-1459 (2014).
Colberg et al. "Pumping insulin during exercise: What healthcare providers and diabetic patients need to know." The physician and sportsmedicine 30(4): 33-38 (2002).
Colmegna et al. "Switched LPV glucose control in type 1 diabetes." IEEE Transactions on Biomedical Engineering 63(6): 1192-1200 (2016).
Dalla-Man et al. "GIM, simulation software of meal glucose—insulin model." Journal of Diabetes Science and Technology1(3): 323-330 (2007).
Dalla-Man et al. "Meal simulation model of the glucose-insulin system." IEEE Transactions on biomedical engineering 54(10): 1740-1749 (2007).
Dalla-Man et al. "The UVA/PADOVA type 1 diabetes simulator: new features." Journal of diabetes science and technology 8(1): 26-34 (2014).
Dassau et al. "Modular artificial β-cell system: a prototype for clinical research." Journal of Diabetes Science and Technology 2(5): 863-872 (2008).
Dassau et al. "In silico evaluation platform for artificial pancreatic β-cell development—a dynamic simulator for closed-loop control with hardware-in-the-loop." Diabetes technology & therapeutics 11(3): 187-194 (2009).
Dassau et al. "Real-time hypoglycemia prediction suite using continuous glucose monitoring: a safety net for the artificial pancreas." Diabetes care 33(6): 1249-1254 (2010).
Davidson et al. "Analysis of guidelines for basal-bolus insulin dosing: basal insulin, correction factor, and carbohydrate-to-insulin ratio." Endocrine Practice 14(9): 1095-1101 (2008).
Del Prato et al. "Effect of sustained physiologic hyperinsulinaemia and hyperglycemia on insulin secretion and insulin sensitivity in man." Diabetologia 37(10): 1025-1035 (1994).
Dobbins et al. "Compartmental modeling of glucagon kinetics in the conscious dog." Metabolism 44(4): 452-459 (1995).
Domanski et al., "Assessment of predictive control performance using fractal measures." Nonlinear Dynamics 89(2): 773-790 (2017).
Doyle III et al. "Closed-loop artificial pancreas systems: engineering the algorithms." Diabetes care 37(5): 1191-1197 (2014).
Eaton et al. "Hepatic removal of insulin in normal man: dose response to endogenous insulin secretion." The Journal of Clinical Endocrinology & Metabolism 56(6): 1294-1300 (1983).
Edgerton et al. "Small increases in insulin inhibit hepatic glucose production solely caused by an effect on glycogen metabolism." Diabetes 50(8): 1872-1882 (2001).
El-Khatib et al. "Adaptive closed-loop control provides blood-glucose regulation using dual subcutaneous insulin and glucagon infusion in diabetic swine." Journal of Diabetes Science and Technology 1(2): 181-192 (2007).
Ellingsen et al. "Safety constraints in an artificial pancreatic β cell: an implementation of model predictive control with insulin on board." Journal of diabetes science and technology 3(3): 536-544 (2009).
Enso "Model Predictive Control and State Estimation", 1-112 (2013).
Eqtami et al. "Event-triggered control for discrete-time systems." Proceedings of the 2010 american control conference. IEEE. 4719-4724 (2010).
Eqtami et al. "Novel event-triggered strategies for model predictive controllers." 2011 50th IEEE Conference on Decision and Control and European Control Conference. IEEE. 1-7 (2011).
Eren-Oruklu et al. "Estimation of future glucose concentrations with subject-specific recursive linear models." Diabetes technology & therapeutics 11(4): 243-253 (2009).
Fernández-Esparrach et al. "Peroral endoscopic anastomotic reduction improves intractable dumping syndrome in Roux-en-Y gastric bypass patients." Surgery for Obesity and Related Diseases 6(1): 36-40 (2009).
Beck et al. "Frequency of morning ketosis after overnight insulin suspension using an automated nocturnal predictive low glucose suspend system." Diabetes Care 37(5): 1224-1229 (2014).

(56) References Cited

OTHER PUBLICATIONS

Turksoy et al. "An Integrated Multivariable Artificial Pancreas Control System", Journal of Diabetes Science and Tech 8(3): 498-507 (2014).
Salehi et al. "Altered islet function and insulin clearance cause hyperinsulinemia in gastric bypass patients with symptoms of postprandial hypoglycemia." The Journal of Clinical Endocrinology & Metabolism 99(6): 2008-2017 (2014).
Sarwar et al. "Hypoglycemia after Roux-en-Y gastric bypass: the BOLD experience." Obesity surgery 24(7): 1120-1124 (2014).
Scavini et al. "Intraperitoneal Insulin Absorption After Lona-Term Intraperitoneal Insulin Therapy." Diabetes care 18(1): 56-59 (1995).
Schaepelynck et al. "A recent survey confirms the efficacy and the safety of implanted insulin pumps during long-term use in poorly controlled type 1 diabetes patients." Diabetes technology & therapeutics 13(6): 657-660 (2011).
Schauer et al. "Bariatric surgery versus intensive medical therapy for diabetes—3-year outcomes." New England Journal of Medicine 370(21): 2002-2013 (2014).
Schmelzeisen-Redeker et al. "Time delay of CGM sensors: relevance, causes, and countermeasures." Journal of diabetes science and technology 9(5): 1006-1015 (2015).
Seborg et al., "Chapter 20, Model Predictive Control", Process Dynamics and Control: 414-438 (2011).
Seita et al. "Development of canine models of type 1 diabetes with partial pancreatectomy and the administration of streptozotocin." Cell Medicine 6.(1-2): 25-31 (2013).
Shahriari et al. "Taking the human out of the loop: A review of Bayesian optimization." Proceedings of the IEEE 104(1): 148-175 (2015).
Shapiro et al. "An analysis of variance test for normality (complete samples)." Biometrika 52(3/4): 591-611 (1965).
Soon-Shiong et al. "Successful reversal of spontaneous diabetes in dogs by intraperitoneal microencapsulated islets." Transplantation 54(5): 769-774 (1992).
Soru et al., "MPC based artificial pancreas: strategies for individualization and meal compensation." Annual Reviews in Control 36.1 (2012): 118-128.
Spaan et al. "Implantable insulin pumps: an effective option with restricted dissemination." The Lancet Diabetes & Endocrinology 2(5): 358-360 (2014).
Steil et al. "Automated insulin delivery for type 1 diabetes." Current Opinion in Endocrinology, Diabetes and Obesity 13(2): 205-211 (2006).
Steil et al. "Feasibility of automating insulin delivery for the treatment of type 1 diabetes." Diabetes 55(12): 3344-3350 (2006).
Szücs et al. "A memory-efficient representation of explicit MPC solutions." 2011 50th IEEE Conference on Decision and Control and European Control Conference. IEEE. 1916-1921 (2011).
Tarin et al. "Comprehensive pharmacokinetic model of insulin glargine and other insulin formulations." IEEE Transactions on Biomedical Engineering 52(12): 1994-2005 (2005).
Tauschmann et al. "Day-and-night hybrid closed-loop insulin delivery in adolescents with type 1 diabetes: a free-living, randomized clinical trial." Diabetes Care 39(7): 1168-1174 (2016).
Thabit et al. "Home use of an artificial beta cell in type 1 diabetes." New England Journal of Medicine 373(22): 2129-2140 (2015).
Thabit et al. "Coming of age: the artificial pancreas for type 1 diabetes." Diabetologia 59(9): 1795-1805 (2016).
Toffanin et al. "Dynamic insulin on board: incorporation of circadian insulin sensitivity variation." Journal of diabetes science and technology 7(4): 928-940 (2013).
Toffanin et al. "Artificial pancreas: model predictive control design from clinical experience." Journal of Diabetes Science and Technology 7(6): 1470-1483 (2013).
Toffanin et al. "Toward a run-to-run adaptive artificial pancreas: In silico results." IEEE Transactions on Biomedical Engineering 65(3): 479-488 (2017).
Trimpe et al. "A self-tuning LQR approach demonstrated on an inverted pendulum." IFAC Proceedings vols. 47(3): 11281-11287 (2014).
Trogmann et al. "Hybrid control of type 1 diabetes bolus therapy." 49th IEEE Conference on Decision and Control (CDC). IEEE. 4721-4726 (2010).
Turksoy et al. "Multivariable adaptive identification and control for artificial pancreas systems." IEEE Transactions on Biomedical Engineering 61(3): 883-891 (2013).
Turksoy et al. "Adaptive control of artificial pancreas systems—a review." Journal of healthcare engineering 5(1): 1-22 (2014).
Tvarijonaviciute et al. "Obesity-related metabolic dysfunction in dogs: a comparison with human metabolic syndrome." BMC Veterinary Research 8(1): 1-8 (2012).
Tyagounov. "High-performance model predictive control for process industry." Technische Universiteit Eindhoven, Eindhoven, Netherlands (2004).
Valderas et al. "Acarbose improves hypoglycaemia following gastric bypass surgery without increasing glucagon-like peptide 1 levels." Obesity surgery 22(4): 582-586 (2012).
Van Bon et al. "Feasibility of a portable bihormonal closed-loop system to control glucose excursions at home under free-living conditions for 48 hours." Diabetes technology & therapeutics 16(3): 131-136 (2014).
Van Dijk et al. "Intraperitoneal insulin infusion: treatment option for type 1 diabetes resulting in beneficial endocrine effects beyond glycaemia." Clinical endocrinology 81(4): 488-497 (2014).
Van Dijk et al. "Continuous intraperitoneal insulin infusion versus subcutaneous insulin therapy in the treatment of type 1 diabetes: effects on glycemic variability." Diabetes technology & therapeutics 17(6): 379-384 (2015).
Van Dijk et al. "Different effects of intraperitoneal and subcutaneous insulin administration on the GH-IGF-1 axis in type 1 diabetes." The Journal of Clinical Endocrinology & Metabolism 101(6): 2493-2501 (2016).
Van Heusden et al., "Control-Relevant Models for Glucose Control Using a priori patient characteristics." IEEE transactions on biomedical engineering 59(7): 1839-1849 (2011).
Vukmir et al. "Glucagon: prehospital therapy for hypoglycemia." Annals of emergency medicine 20(4): 375-379 (1991).
Wang et al. "Closed-loop control of artificial pancreatic beta-cell in type 1 diabetes mellitus using model predictive iterative learning control." IEEE Transactions on Biomedical Engineering 57(2): 211-219 (2009).
Wang et al. "Survey on iterative learning control, repetitive control, and run-to-run control." Journal of Process Control 19(10): 1589-1600 (2009).
Wang et al., "Automatic Bolus and Adaptive basal algorithm for the artificial pancreatic β-cell." Diabetes technology & therapeutics 12(11): 879-887 (2010).
Wang et al. ""Learning" can improve the blood glucose control performance for type 1 diabetes mellitus." Diabetes technology & therapeutics 19(1): 41-48 (2017).
Yeh et al. "Comparative effectiveness and safety of methods of insulin delivery and glucose monitoring for diabetes mellitus: a systematic review and meta-analysis." Annals of internal medicine 157(5): 336-347 (2012).
Yen et al. "Effect of somatostatin in patients with acromegaly: suppression of growth hormone, prolactin, insulin and glucose levels." New England Journal of Medicine 290(17): 935-938 (1974).
Zavitsanou et al. "Embedded control in wearable medical devices: Application to the artificial pancreas." Processes 4(35): 1-29 (2016).
Zisser et al. "Run-to-run control of meal-related insulin dosing." Diabetes technology & therapeutics 7(1): 48-57 (2005).
Zisser et al. "Clinical results of an automated artificial pancreas using technosphere inhaled insulin to mimic first-phase insulin secretion." Journal of diabetes science and technology 9(3): 564-572 (2015).
Ljung. "System identification." Signal analysis and prediction. Birkhäuser, Boston, MA, 163-173 (1998).
Longman. "Iterative learning control and repetitive control for engineering practice." International journal of control 73(10): 930-954 (2000).

(56) References Cited

OTHER PUBLICATIONS

Luo. "Machine learning of lifestyle data for diabetes." The University of Western Ontario. Electronic Thesis and Dissertation Repository, 3650 (2016).
Ly et al. "Day and night closed-loop control using the integrated Medtronic hybrid closed-loop system in type 1 diabetes at diabetes camp." Diabetes Care 38(7): 1205-1211 (2015).
Ly et al. "Automated overnight closed-loop control using a proportional-integral-derivative algorithm with insulin feedback in children and adolescents with type 1 diabetes at diabetes camp." Diabetes technology & therapeutics 18(6): 377-384 (2016).
Ly et al. "Automated hybrid closed-loop control with a proportional-integral-derivative based system in adolescents and adults with type 1 diabetes: individualizing settings for optimal performance." Pediatric diabetes 18(5): 348-355 (2017).
Maahs et al. "A randomized trial of a home system to reduce nocturnal hypoglycemia in type 1 diabetes." Diabetes care 37(7): 1885-1891 (2014).
Maahs et al. "Outcome measures for artificial pancreas clinical trials: a consensus report." Diabetes care 39(7): 1175-1179 (2016).
Magni et al. "Model predictive control of type 1 diabetes: an in silico trial." Journal of Diabetes Science and Technology 1:(6) 804-812 (2007).
Magni et al. "Evaluating the efficacy of closed-loop glucose regulation via control-variability grid analysis." Journal of diabetes science and technology 2(4): 630-635 (2008).
Matsuo et al. "Strict glycemic control in diabetic dogs with closed-loop intraperitoneal insulin infusion algorithm designed for an artificial endocrine pancreas." Journal of Artificial Organs 6(1): 55-63 (2003).
Mclaughlin et al. "Reversible hyperinsulinemic hypoglycemia after gastric bypass: a consequence of altered nutrient delivery." The Journal of Clinical Endocrinology & Metabolism 95(4): 1851-1855 (2010).
Mehta et al. "Impact of carbohydrate counting on glycemic control in children with type 1 diabetes." Diabetes Care 32(6): 1014-1016 (2009).
Messori et al., "A constrained model predictive controller for an artificial pancreas." IFAC Proceedings vols. 47(3):10144-10149 (2014).
Mingrone et al. "Bariatric-metabolic surgery versus conventional medical treatment in obese patients with type 2 diabetes: 5 year follow-up of an open-label, single-centre, randomised controlled trial." The Lancet 386(9997): 964-973 (2015).
Moore. "Iterative learning control: An overview." Iterative Learning Control for Deterministic Systems (371): 9-22 (1993).
Moreira et al. "Post-prandial hypoglycemia after bariatric surgery: pharmacological treatment with verapamil and acarbose." Obesity surgery 18(12):1618-1621 (2008).
Myers et al. "Intraportal glucose delivery enhances the effects of hepatic glucose load on net hepatic glucose uptake in vivo." The Journal of clinical investigation 88(1): 158-167 (1991).
Myint et al. "Prolonged successful therapy for hyperinsulinaemic hypoglycaemia after gastric bypass: the pathophysiological role of GLP1 and its response to a somatostatin analogue." European Journal of Endocrinology 166(5): 951-955 (2012).
Newswanger et al. "Development of a highly stable, nonaqueous glucagon formulation for delivery via infusion pump systems." Journal of diabetes science and technology 9(1): 24-33 (2015).
Nimri et al. "MD-Logic overnight control for 6 weeks of home use in patients with type 1 diabetes: randomized crossover trial." Diabetes care 37(11): 3025-3032 (2014).
Norrlöf. "Iterative Learning Control—Analysis, Design, and Experiments." Thesis No. 653, Linkoping Univ., Linkoping, Sweden (2000).
Owens et al. "Run-to-run control of blood glucose concentrations for people with type 1 diabetes mellitus." IEEE Transactions on Biomedical Engineering 53(6): 996-1005 (2006).
Palerm et al. "A run-to-run framework for prandial insulin dosing: handling real-life uncertainty." International Journal of Robust and Nonlinear Control: IFAC-Affiliated Journal 17(13): 1194-1213 (2007).
Palerm et al. "A run-to-run control strategy to adjust basal insulin infusion rates in type 1 diabetes." Journal of process control 18(3-4): 258-265 (2008).
Palerm. "Physiologic insulin delivery with insulin feedback: a control systems perspective." Computer methods and programs in biomedicine102(2): 130-137 (2011).
Panteleon et al. "Quantification of delays associated with intraperitoneal insulin delivery and IV glucose sensing aiming at closed loop insulin delivery." Diabetes vol. 53(1701): Abstract 446-P (2004).
Panteleon et al. "Evaluation of the effect of gain on the meal response of an automated closed-loop insulin delivery system." Diabetes 55(7): 1995-2000 (2006).
Parker et al. "Advanced model predictive control (MPC) for type I diabetic patient blood glucose control." Proceedings of the 2000 American Control Conference. ACC. vol. 5. IEEE. 3483-3487(2000).
Patek et al., "Linear quadratic gaussian-based closed-loop control of type 1 diabetes", Journal of Diabetes Science and Technology 1(6): 834-841 (2007).
Patek et al. "Modular closed-loop control of diabetes." IEEE Transactions on Biomedical Engineering 59(11): 2986-2999 (2012).
Patti et al. "Hypoglycemia after gastric bypass: the dark side of GLP-1." Gastroenterology 146(3): 605-608 (2014).
Patti et al. "Insulin response to oral stimuli and glucose effectiveness increased in neuroglycopenia following gastric bypass." Obesity 23(4): 798-807 (2015).
Pernar et al. "Gastric bypass reversal: a 7-year experience." Surgery for Obesity and Related Diseases 12(8): 1492-1498 (2016).
Pickup. "Insulin pumps," Diabetes technology & therapeutics 18(S1): S22-S28 (2016).
Pinsker et al. "Randomized crossover comparison of personalized MPC and PID control algorithms for the artificial pancreas." Diabetes Care 39(7): 1135-1142 (2016).
Ranjan et al. "Effects of subcutaneous, low-dose glucagon on insulin-induced mild hypoglycaemia in patients with insulin pump treated type 1 diabetes." Diabetes, Obesity and Metabolism 18(4): 410-418 (2016).
Reddy et al. "Metabolic control with the bio-inspired artificial pancreas in adults with type 1 diabetes: a 24-hour randomized controlled crossover study." Journal of diabetes science and technology 10(2): 405-413 (2016).
Renard et al. "Complications of the pump pocket may represent a significant cause of incidents with implanted systems for intraperitoneal insulin delivery." Diabetes Care 17(9): 1064-1066 (1994).
Renard et al. "Insulin underdelivery from implanted pumps using peritoneal route: determinant role of insulin pump compatibility." Diabetes Care 19(8): 812-817 (1996).
Renard et al. "Artificial β-cell: clinical experience toward an implantable closed-loop insulin delivery system." Diabetes & metabolism 32(5): 497-502 (2006).
Renard et al. "Closed-loop insulin delivery using a subcutaneous glucose sensor and intraperitoneal insulin delivery: feasibility study testing a new model for the artificial pancreas." Diabetes care 33(1): 121-127 (2010).
Renard et al. "Lower rate of initial failures and reduced occurrence of adverse events with a new catheter model for continuous subcutaneous insulin infusion: prospective, two-period, observational, multicenter study." Diabetes technology & therapeutics 12(10): 769-773 (2010).
Reubi et al. "Distribution of somatostatin receptors in normal and tumor tissue." Metabolism 39(9): 78-81 (1990).
Richter et al. "Computational complexity certification for real-time MPC with input constraints based on the fast gradient method." IEEE Transactions on Automatic Control 57(6): 1391-1403 (2012).
Rivera et al., "Internal model control: PID controller design." Ind. Eng. Chem. Process Des. Dev. 25: 252-265 (1986).
Rohlfing et al. "Defining the relationship between plasma glucose and HbA1c: analysis of glucose profiles and HbA1c in the Diabetes Control and Complications Trial." Diabetes care 25(2): 275-278 (2002).

(56) References Cited

OTHER PUBLICATIONS

Ruiz et al. "Effect of insulin feedback on closed-loop glucose control: a crossover study." Journal of diabetes science and technology 6(5): (2012): 1123-1130.
Russell et al. "Day and night glycaemic control with a bionic pancreas versus conventional insulin pump therapy in preadolescent children with type 1 diabetes: a randomised crossover trial." The lancet Diabetes & endocrinology 4(3): 233-243 (2016).
Salehi et al. "Blockade of glucagon-like peptide 1 receptor corrects postprandial hypoglycemia after gastric bypass." Gastroenterology 146(3): 669-680 (2014).
Li et al., An Ultra-low-power Medium Access Control Protocol for Body Sensor Network, Engineering in Medicine and Biology 27th Annual Conference 2451-2454 (2005).
McGraw-Hill Dictionary of Scientific & Technical Terms, 6E (Sep. 26, 2002) (2002).

* cited by examiner

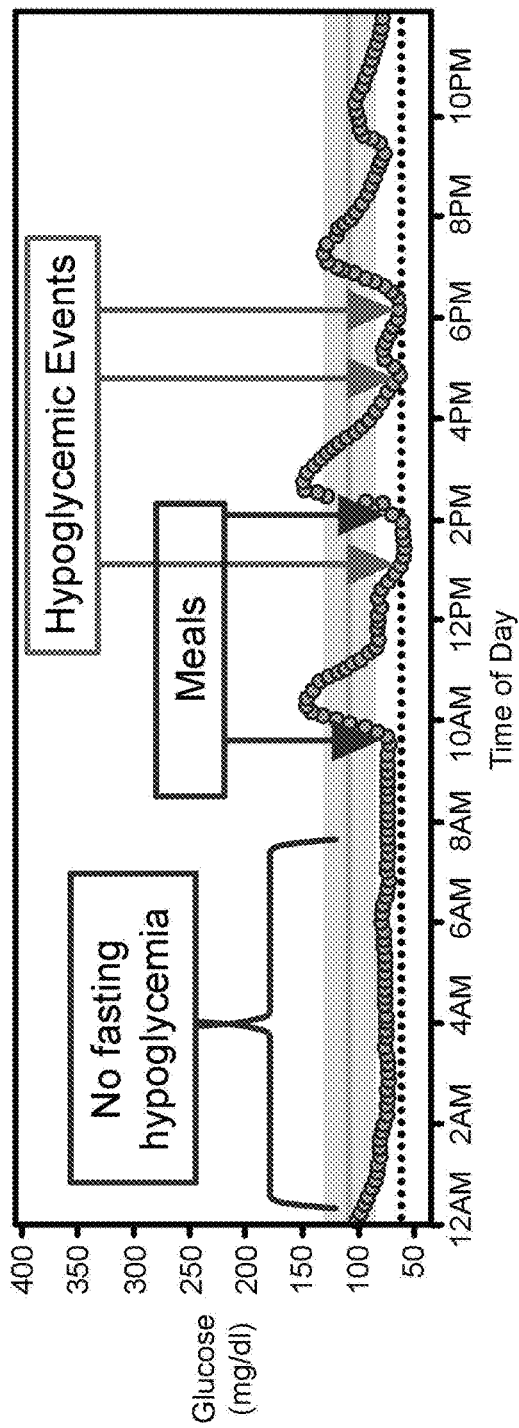 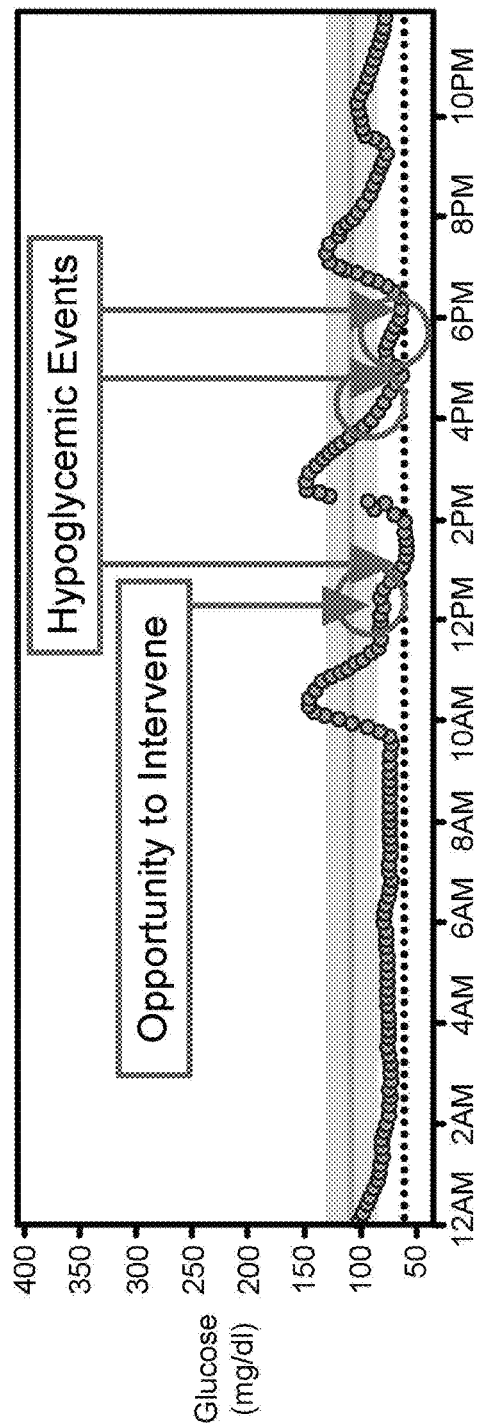
FIG. 1A
FIG. 1B

300B

341. Determine whether HPA is in a non-meal mode and detect when recent ROC measurements >1 mg/dL/min.

342. Switch mode to "waiting for peak."

343. Detect when ROC < 0 mg/dL/min.

344. Switch mode to "waiting for hypoglycemia."

345. Start PBH detection. (Step 410 of FIG 4A).

FIG. 3B

| Stage A  N=2 | Algorithm | LGP algorithm only |
|---|---|---|
| | Glucagon Dose | 150 µg |

| Stage B  N=3 | Algorithm | LGP algorithm and PBH algorithm |
|---|---|---|
| | Glucagon Dose | 150 µg |

| Stage C  N=3 | Algorithm | LGP algorithm and PBH algorithm |
|---|---|---|
| | Glucagon Dose | 300 µg |

| Stage D  N=1 | Algorithm | LGP algorithm and PBH algorithm |
|---|---|---|
| | Glucagon Dose | 1st dose 300 µg, 2nd dose 300 or 150 µg |

FIG. 6

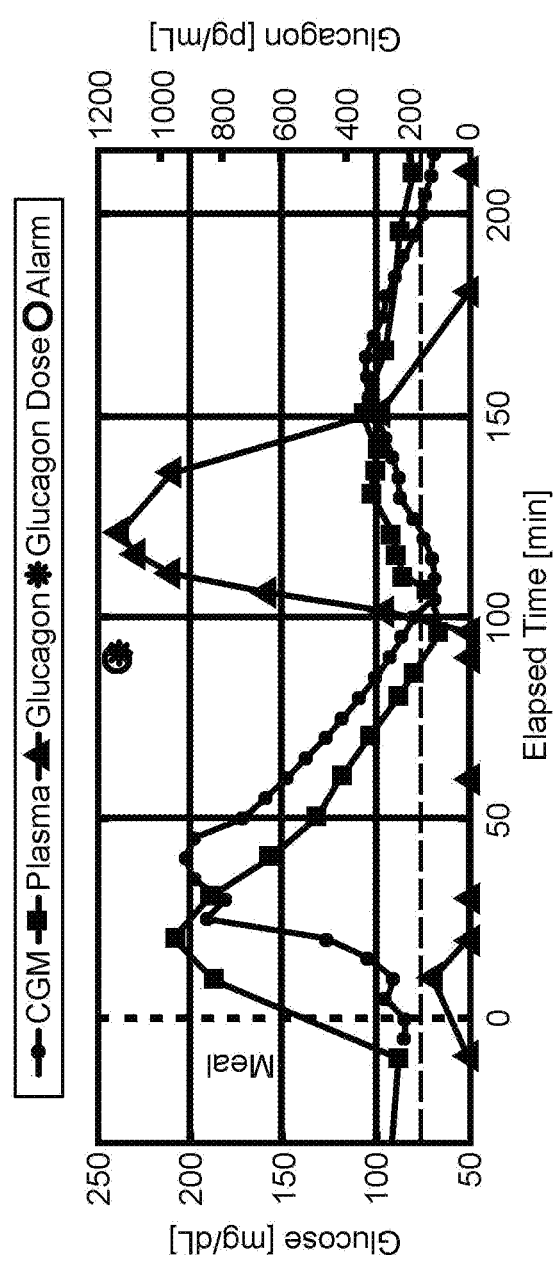
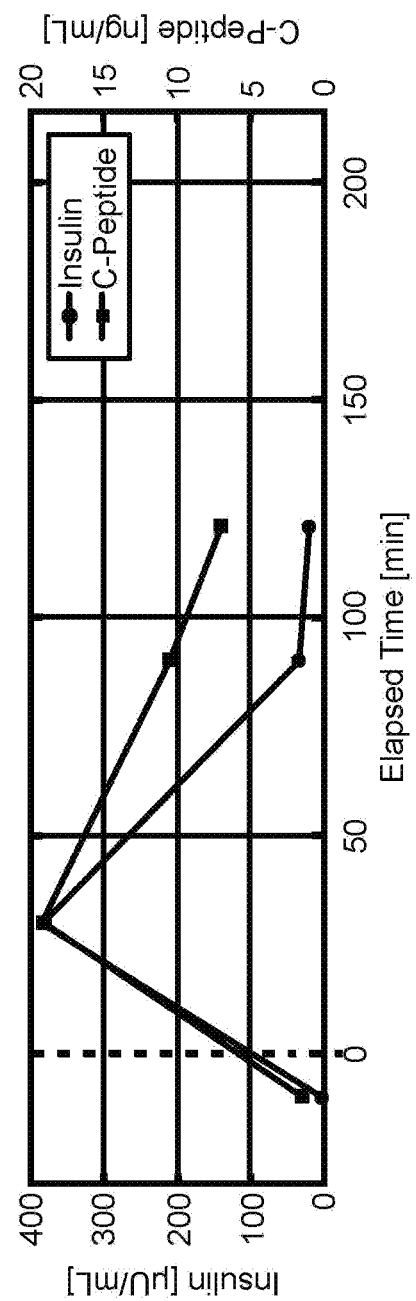
FIG. 8A
FIG. 8B

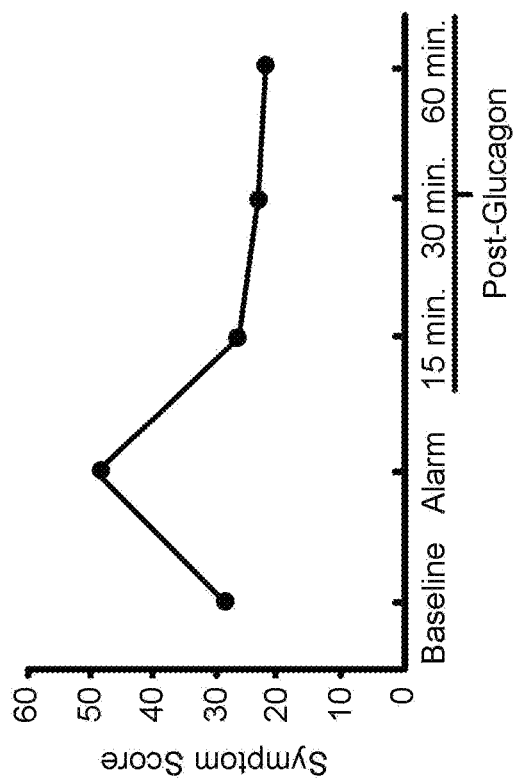
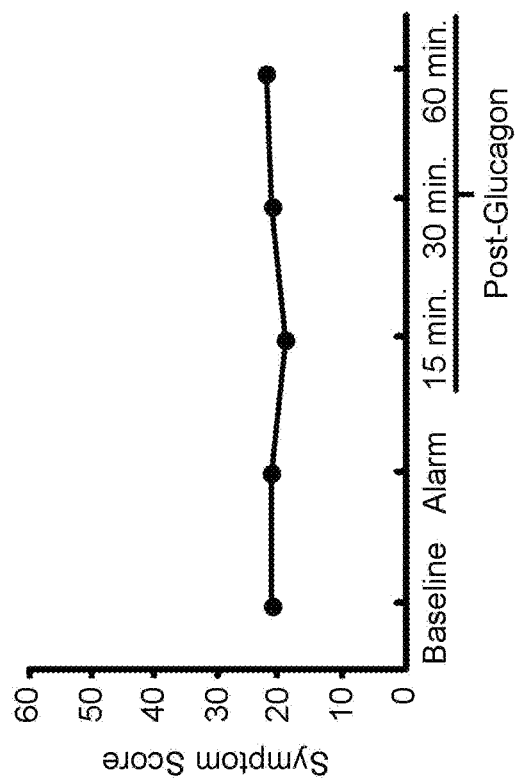
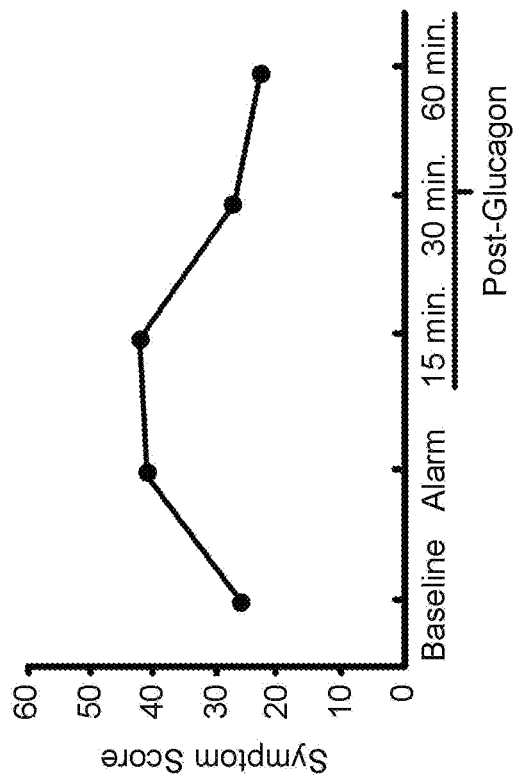
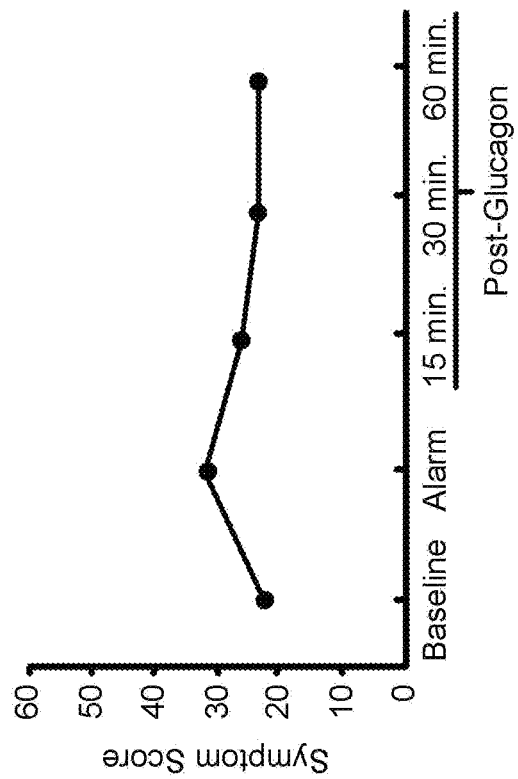
FIG. 12A
FIG. 12B
FIG. 12C
FIG. 12D

PREVENTION OF POST-BARIATRIC HYPOGLYCEMIA USING A NOVEL GLUCOSE PREDICTION ALGORITHM AND MINI-DOSE STABLE GLUCAGON

CROSS REFERENCE TO RELATED APPLICATION

This application claims benefit under 35 U.S.C. § 119(e) of U.S. Provisional Application Ser. No. 62/517,627, filed Jun. 9, 2017, titled "Prevention of Post-Bariatric Hypoglycemia Using a Novel Glucose Prediction Algorithm and Mini-Dose Stable Glucagon," the contents of which are fully incorporated herein by reference in entirety.

STATEMENT REGARDING FEDERALLY SPONSORED RESEARCH

This invention was made with government support under Grant Nos. DK107114 and DK036836 awarded by the National Institutes of Health. The government has certain rights in the invention.

FIELD

The present invention is directed to the field of glucose monitoring and hypoglycemia predictions.

BACKGROUND

The following description includes information that may be useful in understanding the present invention. It is not an admission that any of the information provided herein is prior art or relevant to the presently claimed invention, or that any publication specifically or implicitly referenced is prior art.

Bariatric surgery is a potent tool for the treatment of obesity and type 2 diabetes, resulting in sustained weight loss, improved glycemic control, and improvement in related comorbidities[1-3]. One increasingly recognized complication of bariatric surgery is hypoglycemia, occurring most commonly after roux-en-Y gastric bypass (RYGB) but also reported after vertical sleeve gastrectomy[4]. Up to 75% of patients with history of RYGB have asymptomatic hypoglycemia (<55 mg/dL) by continuous glucose monitoring[5] (CGM), while estimates for severe neuroglycopenia are much lower (range <1 to 10%)[4]. Post-bariatric hypoglycemia (PBH) is characterized by hypoglycemia occurring one to three hours after meals, with increased severity after intake of high glycemic index carbohydrates[6-8]. While the etiology of PBH has not been fully elucidated, excessive incretin and insulin secretion in the postprandial state, reduced insulin clearance[9], and insulin-independent mechanisms are thought to contribute[8,10-12].

Initial therapy for PBH includes medical nutrition therapy to reduce high glycemic index carbohydrates[13]. However, pharmacologic interventions are often required. Acarbose, administered with meals, minimizes the rapid postprandial rise in glucose and insulin, thereby reducing subsequent hypoglycemia[14,15]. Additional treatments include octreotide to reduce incretin and insulin secretion[16], diazoxide and/or calcium channel blockers to reduce insulin secretion[15,17], gastric restriction or banding to slow gastric emptying[18], providing nutrition solely through a gastrostomy tube placed into the bypassed stomach[19], or reversal of bypass[20]. CGM is often helpful to improve safety in patients with hypoglycemic unawareness[21]. Unfortunately, many of these approaches are either poorly tolerated or incompletely effective, even when used in combination. Severe hypoglycemia can be accompanied by syncope, falls, seizures, and cardiac arrhythmias[22]. Hypoglycemia occurring as often as several times per day can lead to hypoglycemic unawareness, reducing safety in driving and employment, reducing autonomy, and causing fear of eating and activity. Thus, there is an urgent need for improved approaches for treatment of severe hypoglycemia to maintain health, allow optimal nutrition, and improve safety.

Glucagon is effective for acute treatment of hypoglycemia in PBH; however, utilization is limited by several shortcomings of traditional glucagon preparations. First, the need for reconstitution of glucagon powder can be daunting for the patient or family members during acute hypoglycemia. Second, glucagon emergency kits are expensive and must be used within 24 hours following reconstitution, limiting each kit to one-time use. Finally, traditional rescue doses of glucagon (0.5-1.0 mg) can cause substantial nausea and rebound hyperglycemia[23]. For example, a constant infusion of glucagon can increase glucose levels above baseline, promoting further insulin secretion after a mixed meal[24]. Therefore, a constant infusion of glucagon can increase the severity of subsequent hypoglycemia[24].

Therefore, present methods do not provide effective real-time detection of hypoglycemia. Nor is there a convenient way to respond with an appropriate dose of glucagon to detection of hypoglycemia.

SUMMARY

Post-bariatric hypoglycemia (PBH) is an increasingly-recognized complication of gastric bypass surgery. Current therapeutic options have suboptimal efficacy. An embodiment of the present disclosure provides for an event-based system that predicts and detects impending hypoglycemia based on continuous glucose monitor (CGM) data and recommends delivery of a mini-dose of liquid glucagon via pump.

The event-based system can provide for continuous glucose monitoring and blood sampling, and glucagon administration via pump delivery system for hypoglycemia. The system performs whether a patient has PBH or neuroglycopenia. The system successfully predicts hypoglycemia through a hypoglycemia prediction algorithm, responds to the detection of impending hypoglycemia by delivering glucagon and can thus prevent prolonged or severe hypoglycemia. Following a meal, the hypoglycemia prediction algorithm successfully can detect impending hypoglycemia. The hypoglycemia prediction algorithm can trigger an alarm, prompting delivery of glucagon (150-300 µg) by a care team or glucagon delivery mechanism. Additionally, higher dosages of glucagon can fully reverse the rapid postprandial falls in glucose characteristic of PBH.

An embodiment of the present disclosure can provide for a method for both predicting and treating hypoglycemia. The method can collect data from at least one sensor. The data can comprise a concentration of glucose in the bloodstream of a subject. The method can then provide for processing the data using a hypoglycemia prediction algorithm (HPA). The method can then provide for predicting impending glucose concentrations using the HPA. The method can then provide for determining whether the predicted glucose concentrations are lower than a hypoglycemic threshold parameter. In response to determining that the predicted glucose concentrations are lower than the hypoglycemic threshold parameter, the method can provide for enacting an impending hypoglycemia protocol.

In some examples, the impending hypoglycemia protocol can comprise sending an alert to the subject and sending a command to a glucagon pump to administer glucagon at an optimal moment. The glucagon pump can be attached to the subject. The command to administer glucagon can contain a dosage amount. The dosage amount can be calculated based on a predicted need of the patient. The impending hypoglycemia protocol further can comprise sending a second command to the glucagon pump to administer a second amount of glucagon at a second optimal moment. The protocol can also comprise sending further glucagon commands at later optimal moments with lower or higher dose of glucagon, as needed.

In some examples, the predicting and determining steps can further include first determining whether a present glucose concentration is in a pre-determined range. In response to determining that the present glucose concentration is in the pre-determined range, the method can provide for calculating a rate of change (ROC) for a set of recent glucose concentrations. The method can then provide for determining whether the rate of change is less than a pre-determined level. In response to determining that the rate of change is less than the pre-determined level, the method can provide for calculating a time to the hypoglycemic threshold parameter based on the calculated rate of change.

In a first instance, the pre-determined range can be any glucose concentration less than 75 mg/dL. The pre-determined ROC level can be −0.1 mg/dL/min.

In a second instance, the pre-determined range can be between 75 and 100 mg/dL. The pre-determined ROC level can be between −0.5 and −5 mg/dL/min.

In another example, the predicting and determining steps can comprise determining whether a present glucose concentration is less than a threshold glucose concentration. In response to determining that the present glucose concentration is less than the threshold glucose concentration, the method can provide for calculating a rate of change for a set of recent glucose concentrations. The method can then provide for determining whether the rate of change is within a threshold range. In response to determining that the rate of change is within the threshold range, the method can provide for calculating a time to the hypoglycemic threshold parameter based on the calculated rate of change. The threshold glucose concentration can be 150 mg/dL. The ROC threshold range is between −0.5 and −5 mg/dL/min.

A second embodiment of the present disclosure can provide a system for outputting an indication of an optimal time to deliver a dose of glucagon. The system can include a glucose sensor, a glucagon pump, a memory, and a control system. The glucose sensor can be configured to output glucose data related to a concentration of glucose in a bloodstream of a patient. The memory can contain machine-readable medium comprising machine executable code having stored thereon instructions for performing a method of delivering the dose of glucagon. The control system can be coupled to the memory and can comprise one or more processors. The control system can be configured to execute the machine executable code to cause the one or more processors conduct a series of steps.

The one or more processors can first store, in the memory, a model for determining an optimal time to inject the dose of glucagon based on a predicted blood glucose level. The one or more processors can then receive, from the glucose sensor, a set of glucose data. The one or more processors can then process the set of glucose data using the model to determine the optimal time to administer the dose of glucagon to the patient. The one or more processors can then send a command to the glucagon pump to administer the dose of glucagon at the optimal time.

In some examples, the processor can be further configured to determine whether the predicted blood glucose level will fall below a threshold within a window of time based on the model. The processor can determine the window of time based on a timestamp of a subset of the set of glucose data that indicates the patient has recently consumed a meal.

The model can be comprised of two modules: (1) a post-prandial hypoglycemia prediction module, designed to predict low glucose levels upon an event detected to be a meal pattern, and (2) a proximity hypoglycemia prediction module, designed to predict low glucose levels.

The proximity hypoglycemia prediction module can predict when the predicted blood glucose level will fall below the predefined hypoglycemic threshold.

In a third embodiment of the present disclosure, a system can output an indication of an optimal time to deliver a dose of glucagon. The system can comprise a glucose sensor, a mobile device, a memory, and a control system. The glucose sensor can be configured to output glucose data related to a concentration of glucose in a bloodstream of a subject. The memory can contain machine readable medium comprising machine executable code having stored thereon instructions for performing a method of delivering a dose of glucagon. The control system can be coupled to the memory and comprise one or more processors. The control system can be configured to execute the machine executable code and cause the one or more processors to conduct a series of steps.

The one or more processors can first store, in the memory, a model for determining the optimal time to inject the dose of glucagon. The one or more processors can then receive, from the glucose sensor, a set of glucose data. The one or more processors can process the set of glucose data using the model to determine an optimal time to inject the dose of glucagon. The one or more processors can then send a command to display a notification on the mobile device at the optimal time to inject the dose of glucagon.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 1A depicts an X-Y plot showing how hypoglycemia can proceed over a day in response to meal events.

FIG. 1B depicts an X-Y plot showing hypoglycemic events and opportunities to intervene before the hypoglycemic events.

FIG. 3B shows an exemplary mode-detection methodology of the hypoglycemia prediction algorithm according to an embodiment of the present disclosure.

FIG. 6 shows a chart of exemplary algorithm methodologies and glucagon dosages according to various embodiments of the present disclosure.

FIG. 8A shows an X-Y plot of time versus glucose concentration in the blood of a subject when a 150 μg glucagon dosage is injected according to an embodiment of the present disclosure.

FIG. 8B shows an X-Y plot of time versus insulin concentration in the blood of a subject when a 150 μg glucagon dosage is injected according to an embodiment of the present disclosure.

FIG. 12A shows an X-Y plot of hypoglycemic symptom scores over time when a 150 μg glucagon dosage is injected according to an embodiment of the present disclosure.

FIG. 12B shows an X-Y plot of hypoglycemic symptom scores over time when a 150 μg glucagon dosage is injected according to an embodiment of the present disclosure.

FIG. 12C shows an X-Y plot of hypoglycemic symptom scores over time when a 300 μg glucagon dosage is injected according to an embodiment of the present disclosure.

FIG. 12D shows an X-Y plot of hypoglycemic symptom scores over time when two glucagon doses are injected according to an embodiment of the present disclosure.

DETAILED DESCRIPTION

Figure 2A:
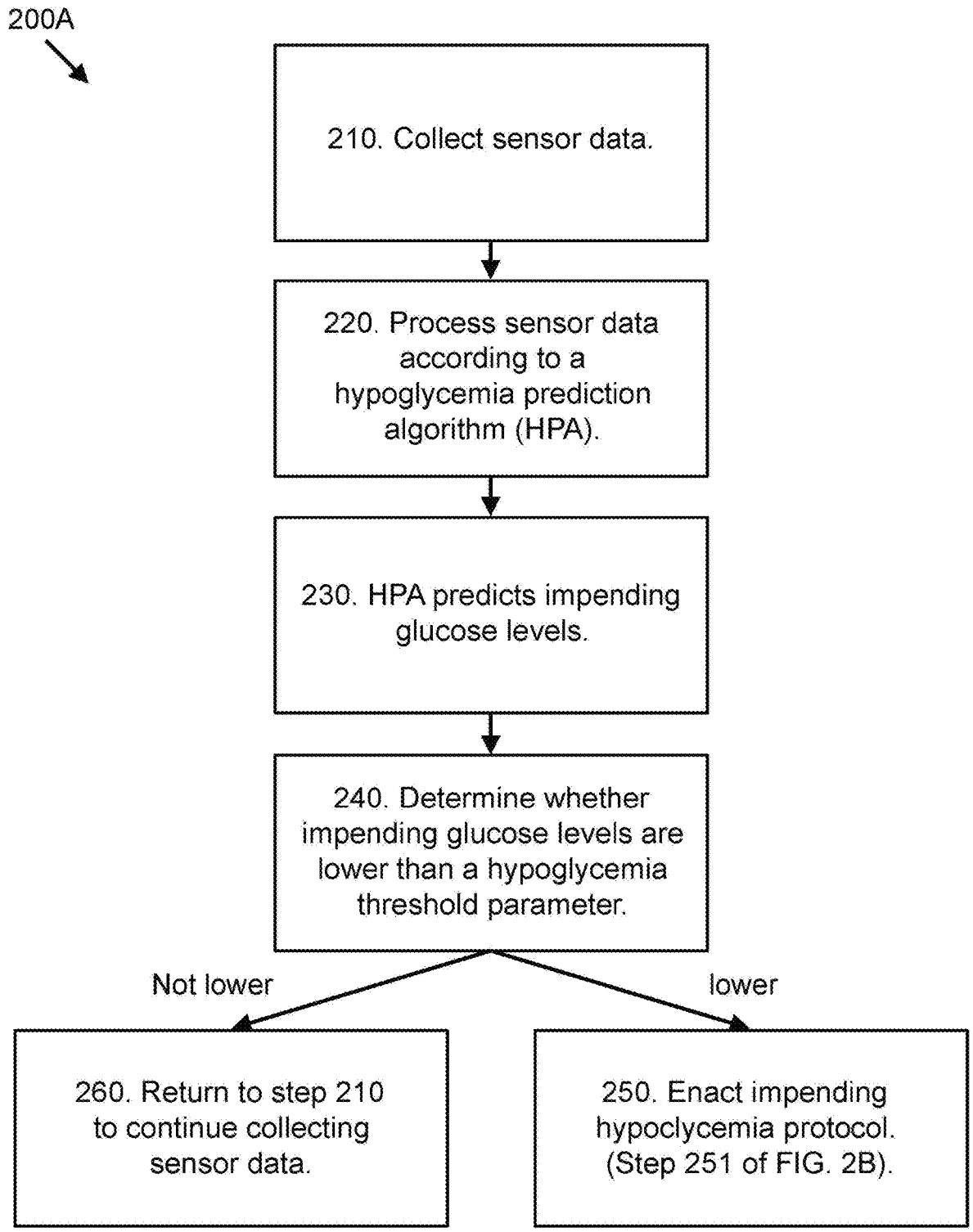
FIG. 2A shows an exemplary methodology for detecting impending hypoglycemia according to an embodiment of the present disclosure.

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

The present disclosure provides for a combination of an automatic hypoglycemia prediction system and a system for fast subcutaneous delivery of a glucagon minidose in response to predicting hypoglycemia. The system can alert a patient or doctor of an impending hypoglycemic event in the near future using continuous glucose level data. The system can also prevent falls in plasma glucose below a predefined threshold (<75 mg/dL). Embodiments of the present disclosure can also prevent severe postprandial hypoglycemia (plasma glucose <60 mg/dL) and avoidance of rebound hyperglycemia (plasma glucose >180 mg/dL) after glucagon delivery. Glucose levels can be monitored by both sensor and plasma samples in real time.

FIG. 1A depicts an X-Y plot showing glucose concentration in a subject versus time of day. The plot shows that an exemplary subject can typically have low glucose levels while the subject is fasting overnight. Meals can show an initial substantial increase in blood glucose levels followed by a substantial decrease. After the first two meal events, depicted in FIG. 1A as close to 10 am and 2 pm, the blood glucose levels drop below a hypoglycemic threshold. FIG. 1A thus shows how meal events can cause severe hypoglycemia occurring multiple times per day.

FIG. 1B depicts an X-Y plot showing the opportunities to intervene before a hypoglycemic event occurs as shown in FIG. 1A. Referring back to FIG. 1B, the opportunities to intervene are when the blood glucose level is lowest but not yet hypoglycemic. Intervening at a low blood glucose level creates the highest probability of avoiding rebound hyperglycemia. Additionally, interventions should occur before hypoglycemia occurs. Intervening in this timeframe prevents the subject from experience the negative effects of hyper- or hypoglycemia.

Embodiments of the Hypoglycemia Prediction Algorithm

FIG. 2A shows an exemplary methodology 200 for detecting impending hypoglycemia according to an embodiment of the present disclosure. The steps of the exemplary method 200 can be performed through a system configured to complete the steps. For example, a computer interface can run software performing the following steps. At step 210, sensor data can be collected. Sensors can collect data on concentration levels from a subject's bloodstream of glucose, insulin, C-peptide, and glucagon.

At step 220, this sensor data can then be processed according to a hypoglycemia prediction algorithm (HPA). The sensor data can be processed in a variety of manners, including cleaning the sensor data for ease of analysis. For example, the sensor data can be run through a noise-spike filter and a low-pass filter. Noise spike filters can remove unwanted signal modifications that data can suffer from during capture, storage, transmission, processing, or conversion. Noise spike filters can remove data noise that is not additive and may affect only a small percentage of the sensor data, but might affect that percentage by a large amount. Low-pass filters can pass signals at an amount lower than a certain cutoff amount. This attenuates the sensor data that has a higher amount than the cutoff amount. Altogether, these filters can smooth the set of data.

Figure 4A:
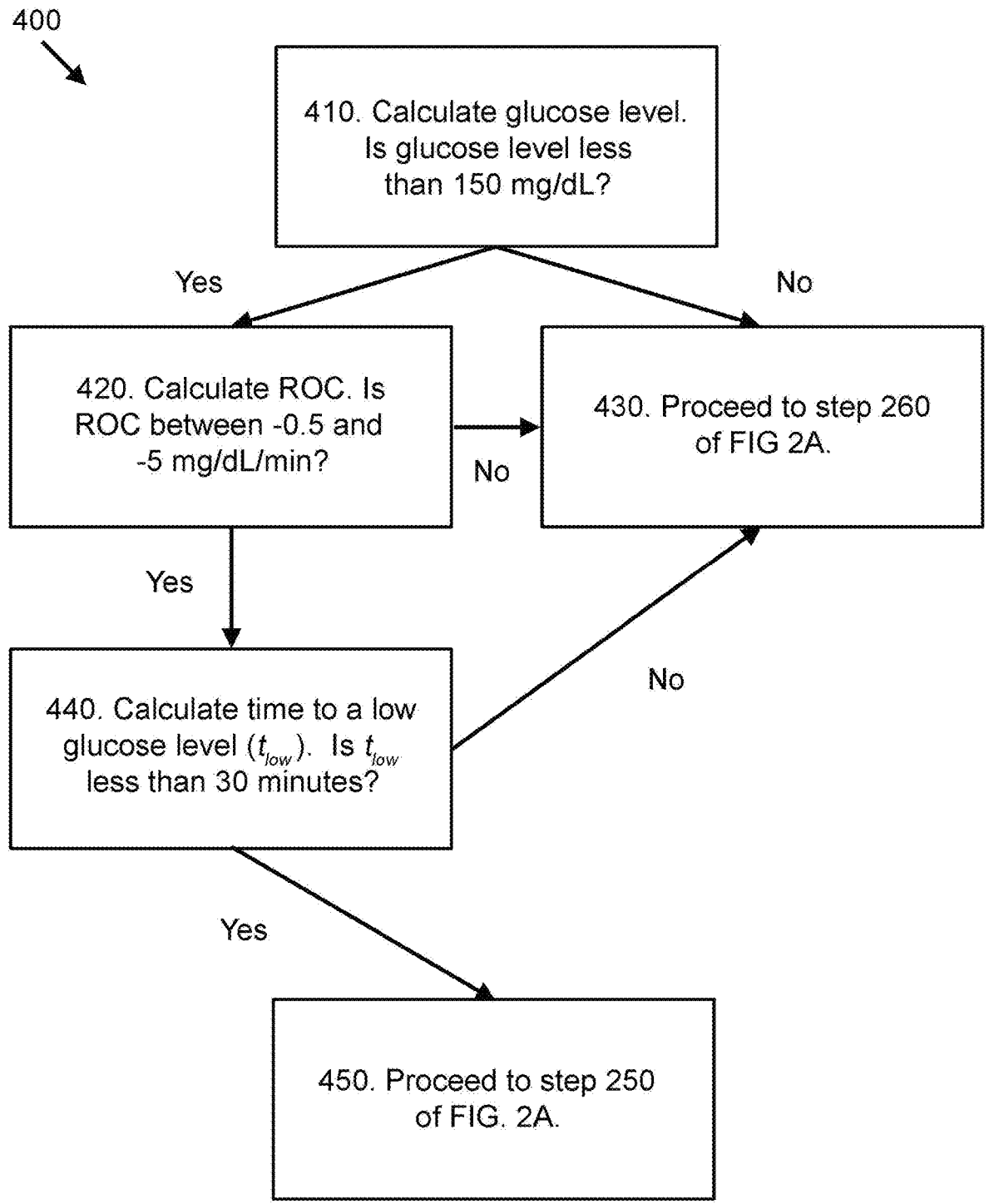
FIG. 4A shows an exemplary post-bariatric hypoglycemia detection methodology according to an embodiment of the present disclosure.
Figure 5A:
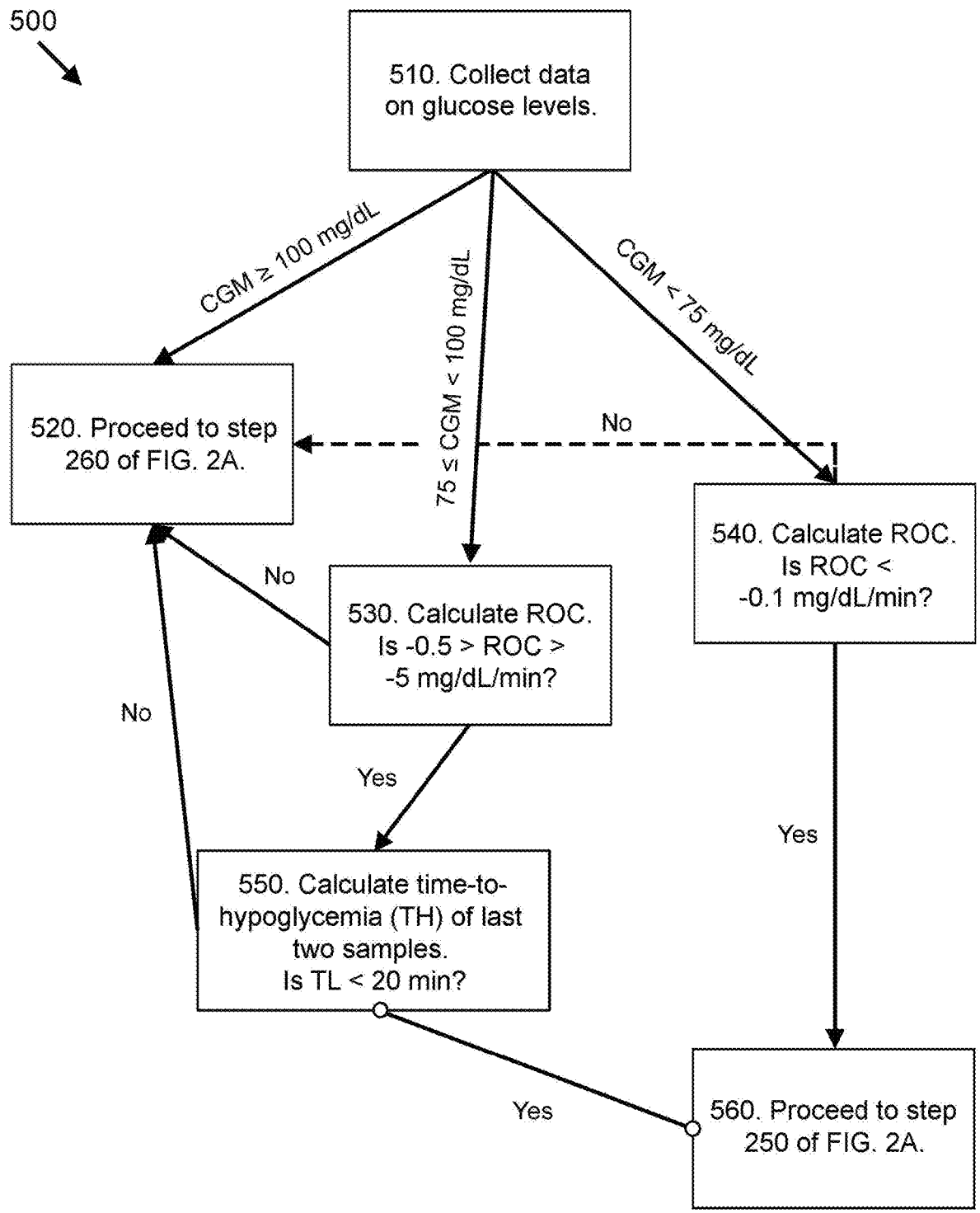
FIG. 5A shows an exemplary low glucose predictor (LGP) methodology according to an embodiment of the present disclosure.

After processing the sensor data, the HPA can predict impending glucose levels in step 230. The HPA can predict impending glucose methods in a variety of ways, including particular examples as shown in FIGS. 4A and 5A. Referring back to FIG. 2A, in one embodiment, the HPA can analyze sensor data history and switch between various modes of operation to predict future glucose levels (discussed further with respect to FIGS. 3A and 3B). In some examples, the HPA can analyze up to two hours of sensor data. In other examples, the HPA can analyze three hours, one hour, or other suitable time periods of data. The HPA can calculate a smoothed version of the rate of change of glucose concentration in the subject's bloodstream using a four-sample moving-average filter. Based on an operation mode and a smoothed-version of the rate of change, the HPA can predict impending glucose levels.

In step 240, the HPA can determine whether impending glucose levels are lower than a hypoglycemic threshold. For example, a hypoglycemic threshold can be 75 mg/dL. In some embodiments, the hypoglycemic threshold can be individually determined based on the subject's particular health data. Impending glucose levels can be the level of predicted glucose concentrations over a certain period of time. For example, the algorithm can examine impending glucose levels for the next thirty minutes.

If the impending glucose levels are predicted to be lower than a hypoglycemic threshold parameter during the certain period of time, then the system can proceed to step 250 which enacts an impending hypoglycemia protocol. An exemplary hypoglycemia protocol is discussed further with respect to FIG. 2B.

Referring back to FIG. 2A, if the impending glucose levels are not predicted to be lower than a hypoglycemic threshold parameter, then the system can proceed to step 260. In step 260, the system can return to step 210 to continue collecting sensor data. Thus, the method 200 provides for an iterative process to continually monitor whether a subject's impending glucose levels are approaching hypoglycemia.

Figure 2B:
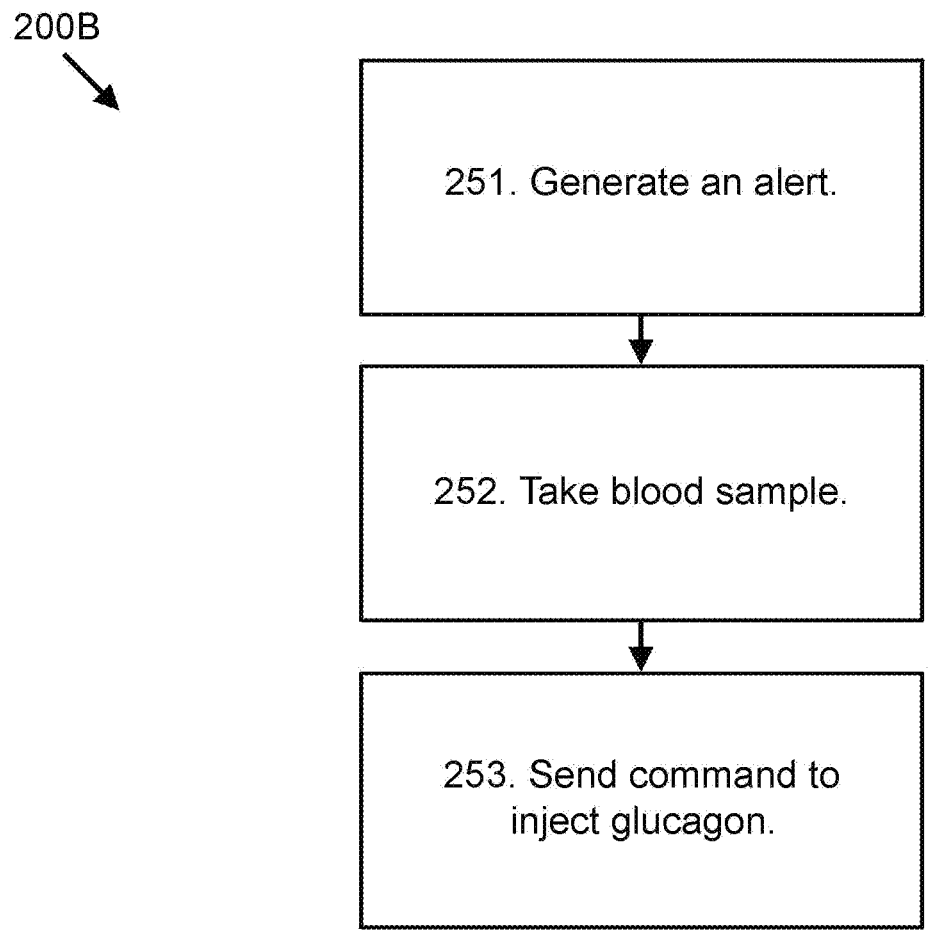
FIG. 2B shows an exemplary protocol in response to detecting impending hypoglycemia according to an embodiment of the present disclosure.

FIG. 2B shows an exemplary impending hypoglycemia protocol 200B according to an embodiment of the present disclosure. This protocol 200B can be enacted after the method 200A hits step 250 in FIG. 2A. Referring back to FIG. 2B, the protocol 200B begins in step 251 by generating an alert. The alert can notify a team of clinicians and/or the subject that the subject will soon experience hypoglycemia. The alert can be a cell-phone notification, an audible sound, a vibration, or any other method without limitation of notifying the subject.

The HPA algorithm can implement a safety "lockout" mechanism that prevents issuing an alarm if a hypoglycemia alert had been issued recently. For example, the lockout mechanism can prevent issuing an alarm for thirty minutes after a recent hypoglycemia alert. If the subject's glucose level was less than 65 mg/dL, the algorithm can prevent issuing an alarm for fifteen minutes after a recent hypoglycemia alert.

After issuing alert, the system can take a blood sample in step 252. The blood sample can identify blood concentrations of biological materials. These materials can include, for example, glucose, insulin, plasma, glucagon, C-peptide, and any other nutrient, protein, and/or hormone in the blood, without limitation. In some embodiments, the system can skip step 252 and proceed directly to step 253.

The system can then proceed to step 253 and send a command to inject glucagon into the patient. The amount of glucagon injected can depend on various biological characteristics of the patient, including data collected from the blood sample in step 252, a patient's weight, BMI, hydration level, and any other biological information, without limitation. For example, based on a patient's predicted need and a glucose profile, a full dose or a partial dose could be determined by the system. Additionally, the system can determine that single or multiple commands can be sent to inject glucagon. For example, the system can determine that a first glucagon dosage should be injected and then a second glucagon dosage. The system can send commands for both a first and second glucagon injection.

Figure 14:
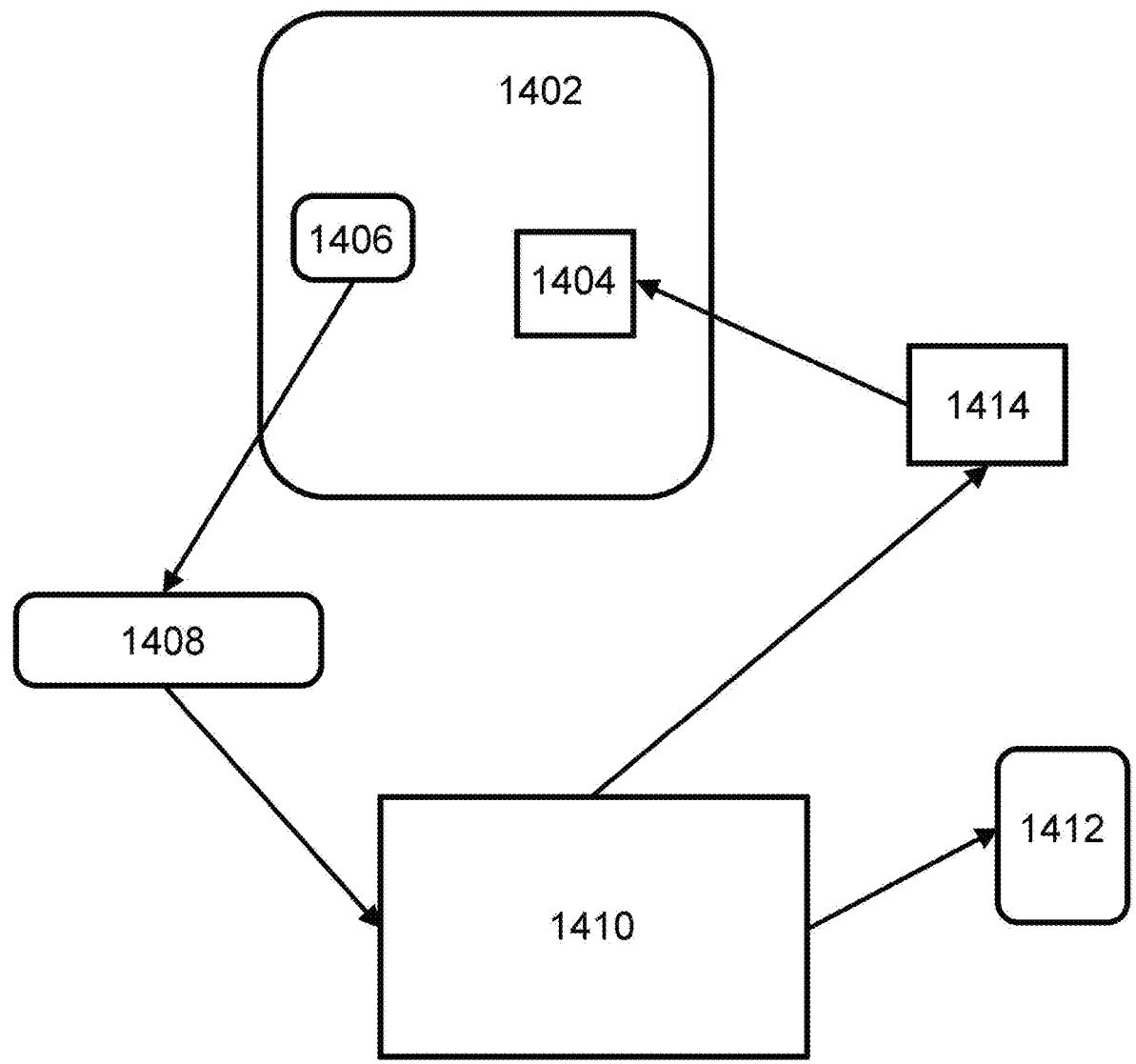
FIG. 14 shows an exemplary glucagon injection system according to an embodiment of the present disclosure.

The system's communication of a command to discuss glucagon and a subsequent injection of glucagon is discussed further with respect to FIG. 14.

Referring back to FIGS. 2A-2B, the figures show an exemplary method of monitoring glucose levels of a patient in real time. The system can constantly review glucose levels of a patient, predict future glucose levels, and identify when a patient will enter hypoglycemia. Accurately detecting impending hypoglycemia allows the system to send a command for an injection of glucagon. Injection of glucagon before the patient actually enters hypoglycemia can prevent the patient from entering hypoglycemia.

Figure 3A:
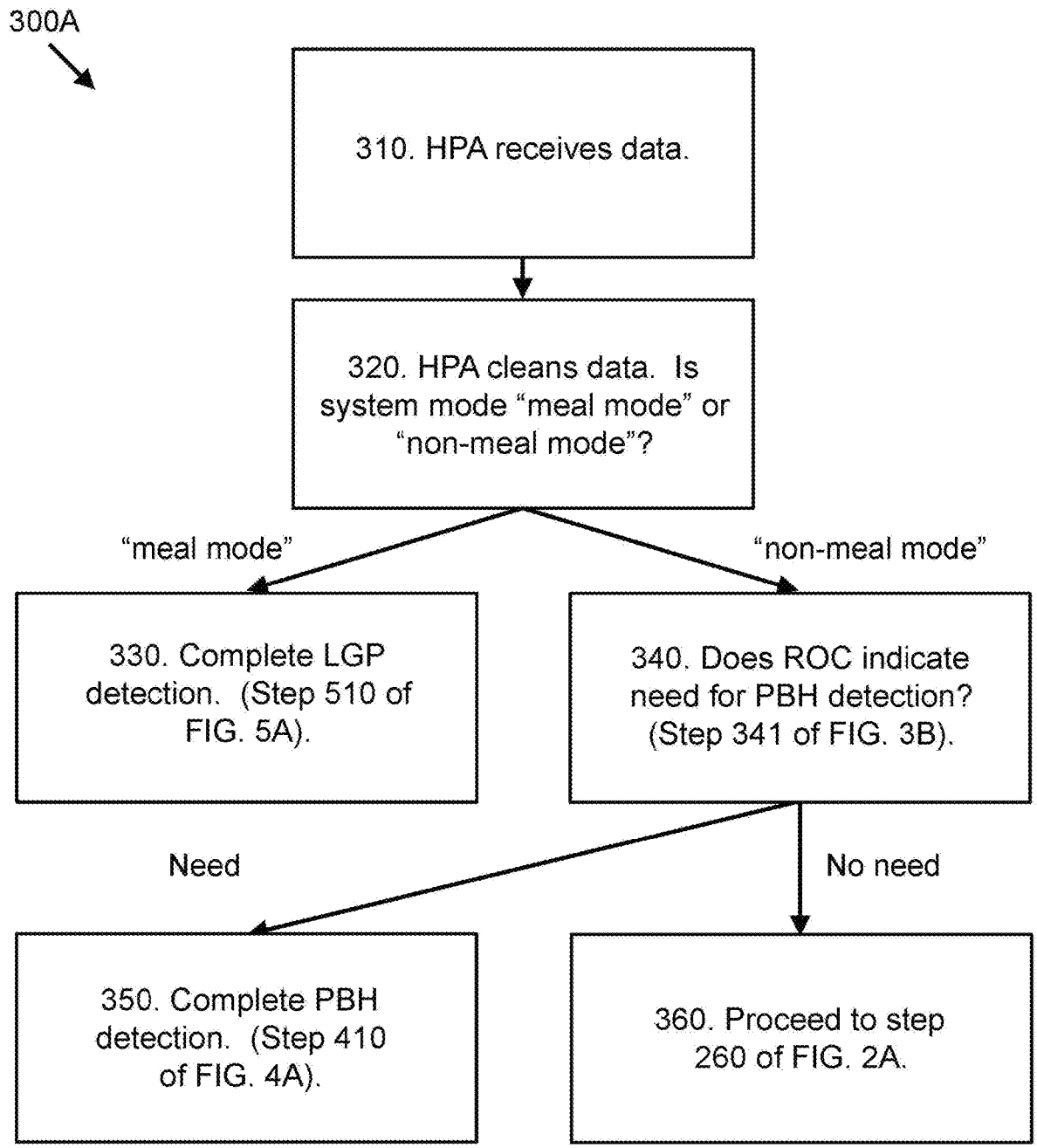
FIG. 3A shows an exemplary hypoglycemia prediction algorithm according to an embodiment of the present disclosure.

FIG. 3A shows an exemplary hypoglycemia prediction algorithm (HPA) 300A according to an embodiment of the present disclosure. The steps of the HPA 300A can be performed through a system configured to complete the steps. For example, a computer interface can run software performing the following steps. At step 310, HPA can receive data. The data can be collected from a biological sensor on the patient. The data can include information on a concentration of glucose in the patient's blood.

In step 320, the HPA can clean the data. For example, the data can be run through a noise-spike filter and a low-pass filter. Noise spike filters can remove unwanted signal modifications that data can suffer from during capture, storage, transmission, processing, or conversion. Noise spike filters can remove data noise that is not additive and may affect only a small percentage of the sensor data, but might affect that percentage by a large amount. Low-pass filters can pass signals at an amount lower than a certain cutoff amount. This attenuates the sensor data that has a higher amount than the cutoff amount. Altogether, these filters can smooth the set of data. Further in step 310, the system can determine whether the system is in a meal mode or a non-meal mode. If the system is in a meal-mode there can be increased chances that the patient will experience post-bariatric hypoglycemia which can occur one to three hours after meals.

Therefore, if the system is in meal-mode, the system will proceed to step 330 and complete Low Glucose Predictor (LGP) detection to identify when the patient's glucose has fallen below a hypoglycemic threshold. An exemplary LGP detection is discussed further with respect to FIG. 5A.

If the system is in a non-meal-mode, the system will proceed to step 340 to identify whether a rate-of-change (ROC) of the patient's glucose concentration indicates a need for PBH detection. An exemplary method for detecting whether there is a need for PBH detection is discussed in FIG. 3B.

If there is a need for PBH detection, the system will proceed to step 350 and complete PBH detection. An exemplary PBH detection is discussed with regards to FIG. 4A.

If there is no need for PBH detection, the system will proceed to step 360. The system can then return to step 260 of FIG. 2A where the system continues to collect sensor data and run the data through the HPA algorithm. By this manner of continually evaluating the data, the system is able to determine whether the patient is predicted to experience hypoglycemia.

FIG. 3B shows an exemplary mode-detection methodology 300B of the hypoglycemia prediction algorithm according to an embodiment of the present disclosure. The methodology begins in step 341 by determining whether the HPA is in a non-meal mode and detecting when recent ROC measurements are greater than 1 mg/dL/min. ROC measurements can be calculated from a set of recent glucose data. If the recent ROC measurements are higher than 1 mg/dL/min, this indicates that the glucagon concentration in the patient is increasing.

The system can then switch its mode to "waiting for peak" in step 342. When the system 300B is in a "waiting for peak" mode, the system is monitoring the ROC measurements until the ROC becomes negative. A negative ROC indicates that the glucagon concentration of the patient's blood is falling.

After switching to a "waiting for peak" mode, the system can proceed to step 343. In step 343, the system detects when the ROC is negative, or below 0 mg/dL/min. After detecting a negative ROC, the system proceeds to step 344 where the mode is switched to "waiting for hypoglycemia." When the ROC is negative, it is likely that the glucagon concentration can fall below a threshold amount. Therefore, a glucagon monitoring system should detect negative ROC in order to closely monitor the glucagon concentration in the patient's blood. Lastly, the system can start PBH detection in step 345. An exemplary PBH detection according to an embodiment of the present disclosure is discussed further with regards to FIG. 4A.

Therefore, methodology 300B provides advantages over current systems through its detection of rising and falling ROC which allows it to accurately predict the rise and fall of a patient's glucagon concentration.

FIG. 4A shows an exemplary PBH detection methodology 400 according to an embodiment of the present disclosure. The methodology 400 starts in step 410 by calculating the glucose level from a patient's data and determining whether the glucose level is less than preliminary detection threshold. For example, the detection threshold can be 150 mg/dL. Having a glucose level higher than the preliminary detection threshold indicates that no action needs to be taken and the system can continue to monitor the glucose levels of the patient.

If the calculated glucose level is higher than the preliminary detection threshold, the system can proceed to step 430. In step 430, the system then goes to step 260 of FIG. 2A and continues monitoring the glucose level of the patient. If the calculated glucose level is lower than the preliminary detection threshold, the system can proceed to step 420. At step 420, the system calculates the ROC from a set of recent glucose data. The system then determines whether the ROC is between −0.5 and −5 mg/dL/min. If the ROC is not in this range, the system goes to step 430, and in turn, to continue monitoring the glucose level of the patient.

An ROC in the range of −0.5 and −5 mg/dL/min shows that the patient's glucose levels are falling quickly. If the ROC is in this range, the system proceeds to step 440. At step 440, the system calculates the time to a low glucose level, $t_{low}$. $T_{low}$ can be the period of time that it will take for the glucose concentration to fall below a hypoglycemic threshold. The system then detects whether $t_{low}$ is less than a threshold period of time. For example, the threshold period of time can be thirty minutes. The threshold period of time can be any period of time which is beyond an accurate prediction of impending glucose levels. If $t_{low}$ is not less than 30 minutes, then the system proceeds to step 430, and in turn, to continue monitoring the glucose level of the patient.

If $t_{low}$ is less than the threshold period of time, the system can proceed to step 450. At step 450, the method can enact an impending hypoglycemia protocol. An exemplary impending hypoglycemia protocol, according to an embodiment of the present disclosure, is discussed further with respect to step 250 of FIG. 2A.

Figure 4B:
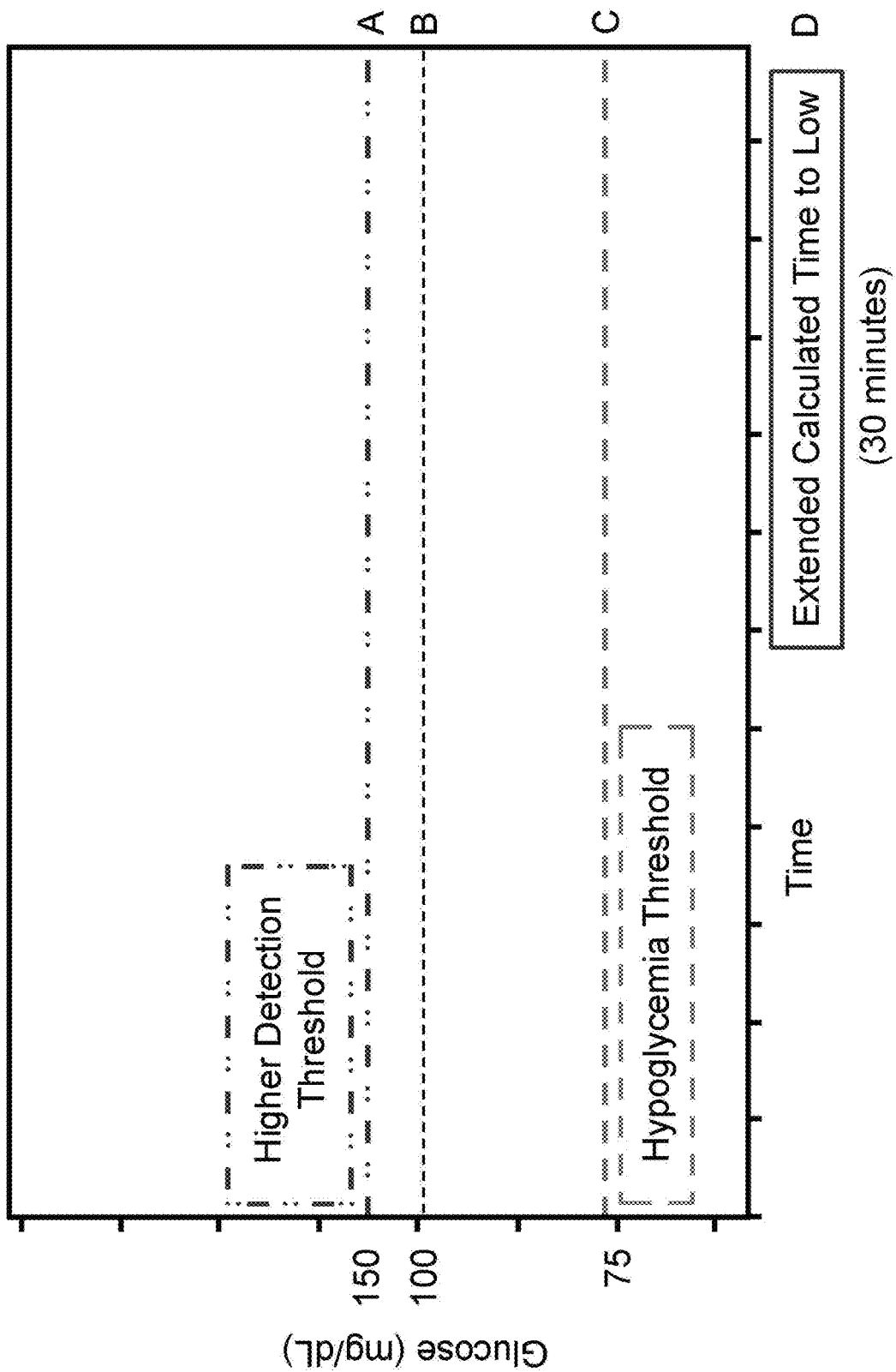
FIG. 4B shows an X-Y plot of an exemplary detection threshold and a hypoglycemic threshold according to an embodiment of the present disclosure.

FIG. 4B shows an X-Y plot of an exemplary detection threshold and a hypoglycemic threshold according to an embodiment of the present disclosure. FIG. 4B shows that the PBH detection algorithm shown in FIG. 4A has a higher detection threshold than the LGP detection algorithm (shown in FIG. 5B). The higher detection threshold allows the system an extended period of time to calculate $t_{low}$ and greater opportunity to warn the patient.

FIG. 5A shows an exemplary low glucose predictor methodology 500 according to an embodiment of the present disclosure. The method 500 begins in step 510 where the system can collect data on glucose levels. If current glucose levels are greater than or equal to 100 mg/dL, then the system proceeds to step 520, and in turn, to continue monitoring the glucose level of the patient.

If the current glucose levels are between 75 mg/dL and 100 mg/dL, then the system proceeds to step 530 where the ROC is calculated. If the ROC is not between −0.5 and −5 mg/dL/min, then the system proceeds to step 520, and in turn, to continue monitoring the glucose level of the patient. If, however, the ROC is between −0.5 and −5 mg/dL/min, then the system proceeds to step 550 to calculate TH, or the time to hypoglycemia. If TH is less than a threshold alarm period, then the system proceeds to step 560 and enacts an impending hypoglycemia protocol. An exemplary impending hypoglycemia protocol is enacted with respect to step 250 of FIG. 2A. If TH is not less than a threshold alarm period, then the system proceeds to step 520, and in turn, to continue monitoring the glucose level of the patient.

Referring back to step 510, if the current glucose levels were less than 75 mg/dL, the system immediately calculates the ROC based on recent glucose data. If the ROC is less than −0.1 mg/dL/min, then the system proceeds directly to enact an impending hypoglycemia protocol in step 560. An exemplary impending hypoglycemia protocol is enacted with respect to step 250 of FIG. 2A.

Therefore, the present system provides a method of detecting glucose levels and rates of change of the glucose levels to determine a response. If the glucose levels are sufficiently high enough and the rates of change insufficient to suggest impending hypoglycemia, the system is equipped to continue monitoring glucose levels. However, if the glucose levels are low enough and/or the rate of change suggests impending hypoglycemia, then the system can enact an impending hypoglycemia protocol and respond quickly to the situation.

Figure 5B:
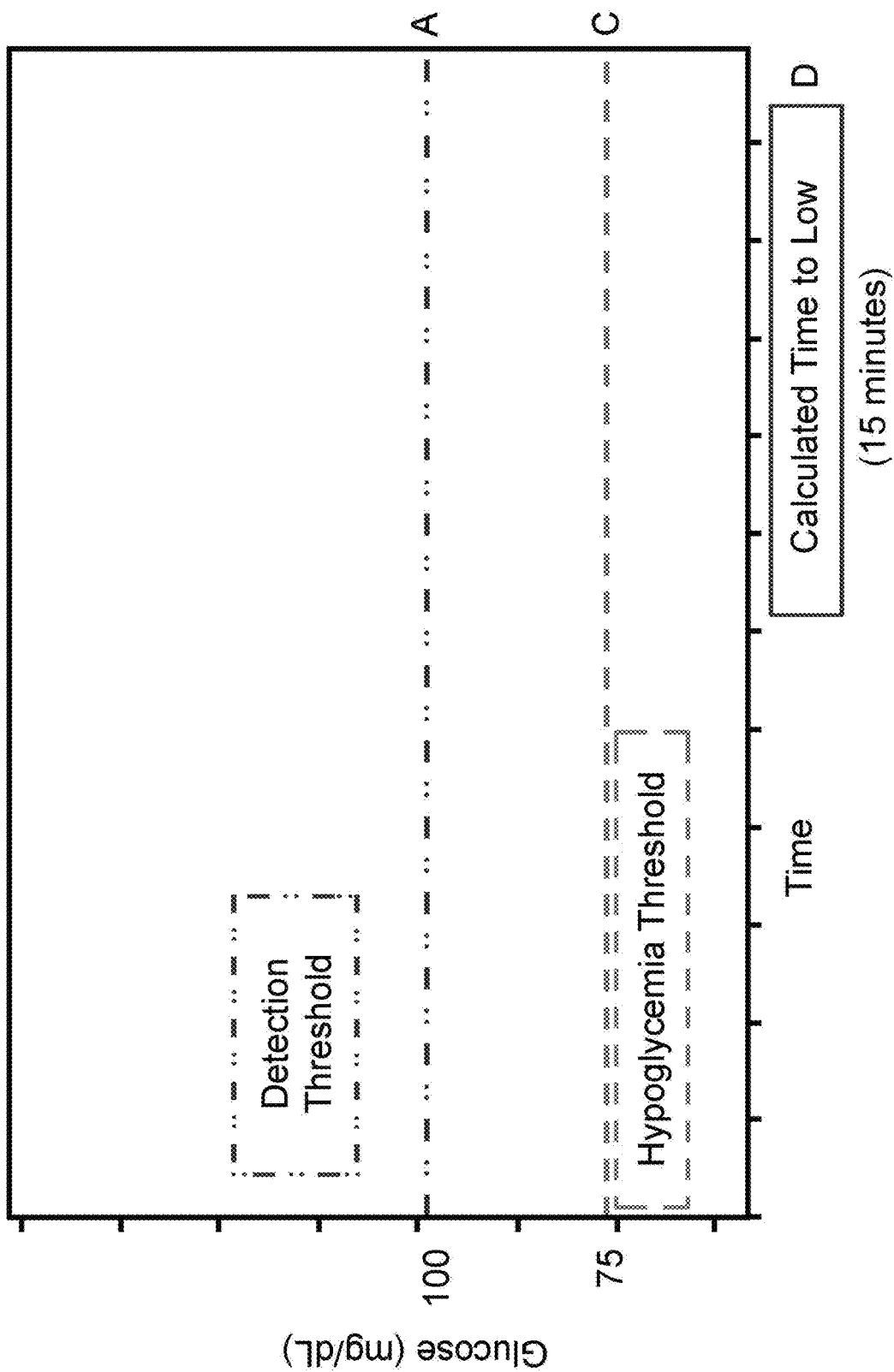
FIG. 5B shows an X-Y plot of an exemplary detection threshold and a hypoglycemic threshold according to an embodiment of the present disclosure.

FIG. 5B shows an X-Y plot of an exemplary detection threshold and a hypoglycemic threshold according to an embodiment of the present disclosure. FIG. 5B shows that the LGP methodology 500 allows a fifteen-minute notification of impending hypoglycemia. Notably, the LGP method has a lower calculated time to low than the PBH method discussed with respect to FIGS. 4A-4B. Therefore, a method which works with both LGB and PBH detection can provide the best support for a patient.

Embodiments of HPA

FIG. 6 shows a chart of exemplary algorithm methodologies and glucagon dosages according to various embodiments of the present disclosure. These exemplary methodologies are referred to in subsequent charts. Stage A refers to an exemplary study conducted according to an embodiment of the present disclosure where the HPA relies on only LGP detection. Stage A also provides to subjects a glucagon dose of 150 μg. Stage A had two participants in the exemplary study conducted according to an embodiment of the present disclosure.

Stage B refers to an exemplary study conducted according to an embodiment of the present disclosure where HPA relies on both LGP detection and PBH detection. Stage B provides to subjects a glucagon dose of 150 μg. Stage B had three participants in the exemplary study conducted according to an embodiment of the present disclosure.

Stage C refers to an exemplary study conducted according to an embodiment of the present disclosure where the HPA relies on both LGP detection and PBH detection. Stage C provides to subjects a glucagon dose of 300 μg. Stage C had three participants in the exemplary study conducted according to an embodiment of the present disclosure.

Stage D refers to an exemplary study conducted according to an embodiment of the present disclosure where the HPA relies on both LGP detection and PBH detection. Stage D provides to subjects a first glucagon dose of 300 μg and a second glucagon dose of either 300 or 150 μg. Stage D had one participant in the exemplary study conducted according to an embodiment of the present disclosure.

Figure 7A:
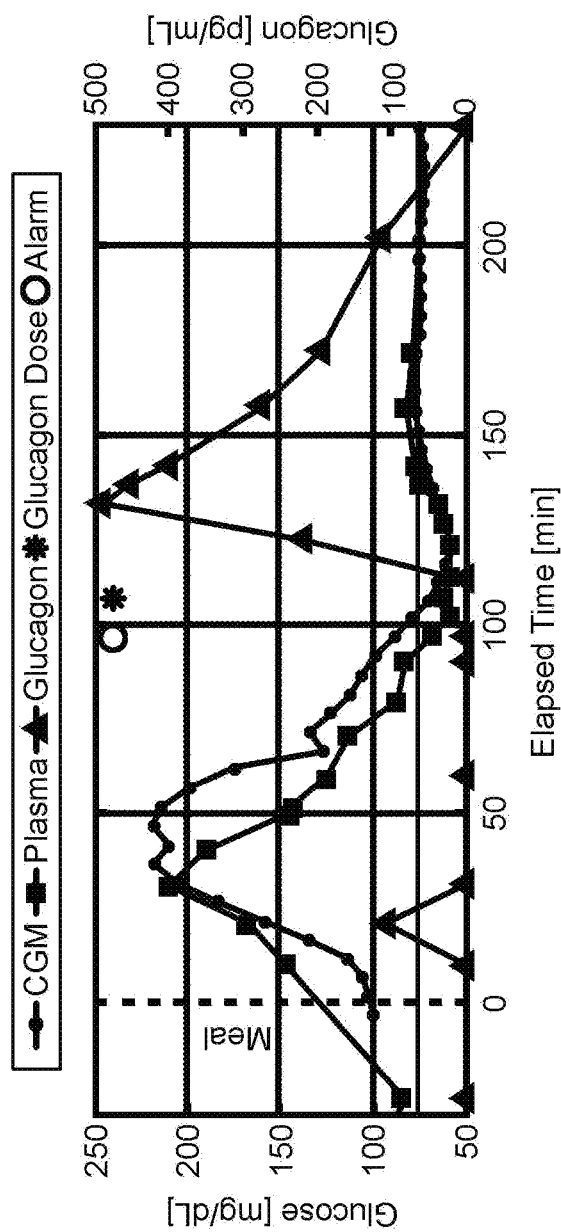
FIG. 7A shows an X-Y plot of time versus glucose concentration in the blood of a subject when a 150 μg glucagon dosage is injected according to an embodiment of the present disclosure.
Figure 7B:
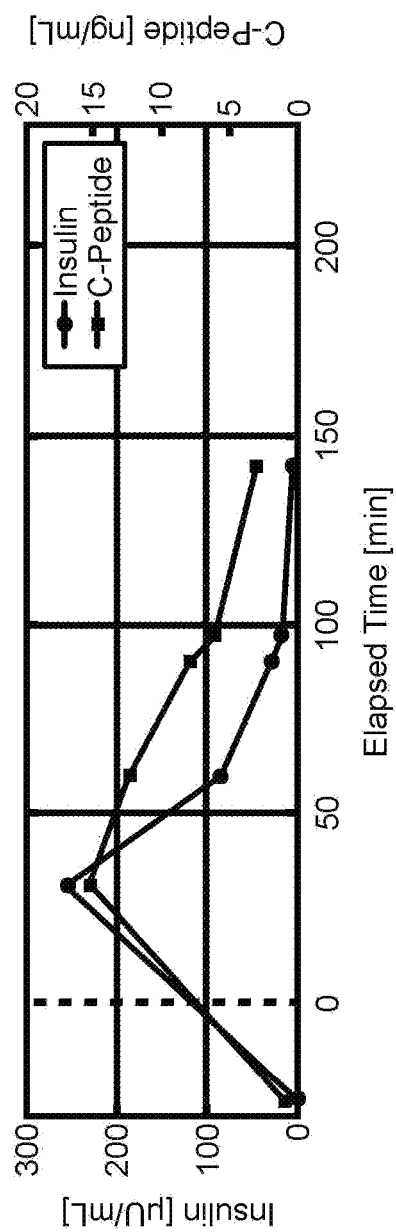
FIG. 7B shows an X-Y plot of time versus insulin concentration in the blood of a subject when a 150 μg glucagon dosage is injected according to an embodiment of the present disclosure.
Figure 9A:
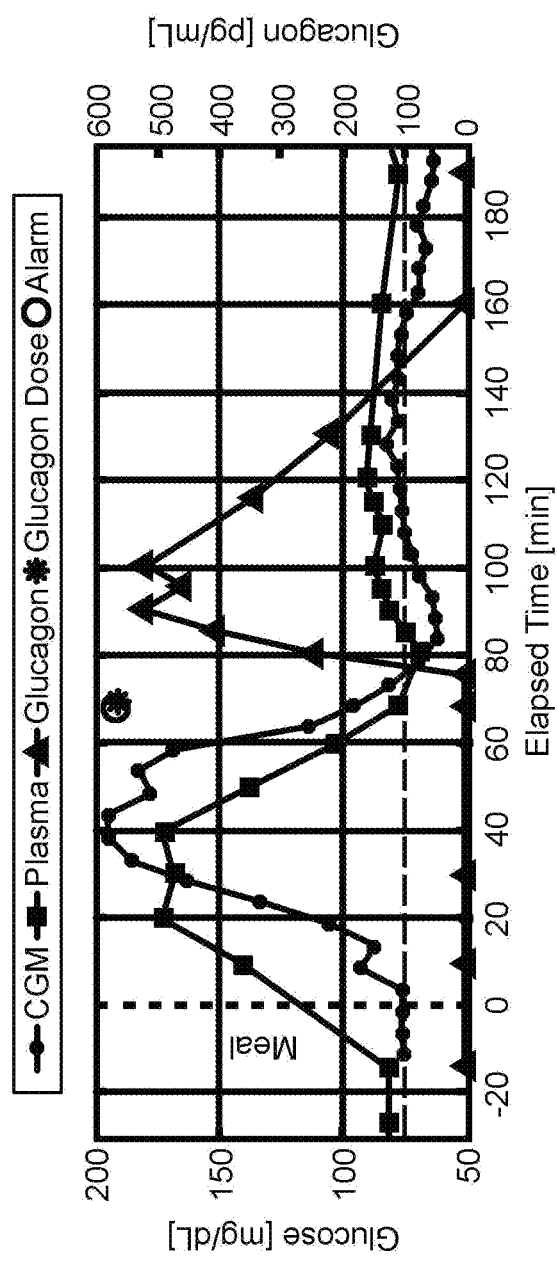
FIG. 9A shows an X-Y plot of time versus glucose concentration in the blood of a subject when a 300 μg glucagon dosage is injected according to an embodiment of the present disclosure.
Figure 9B:
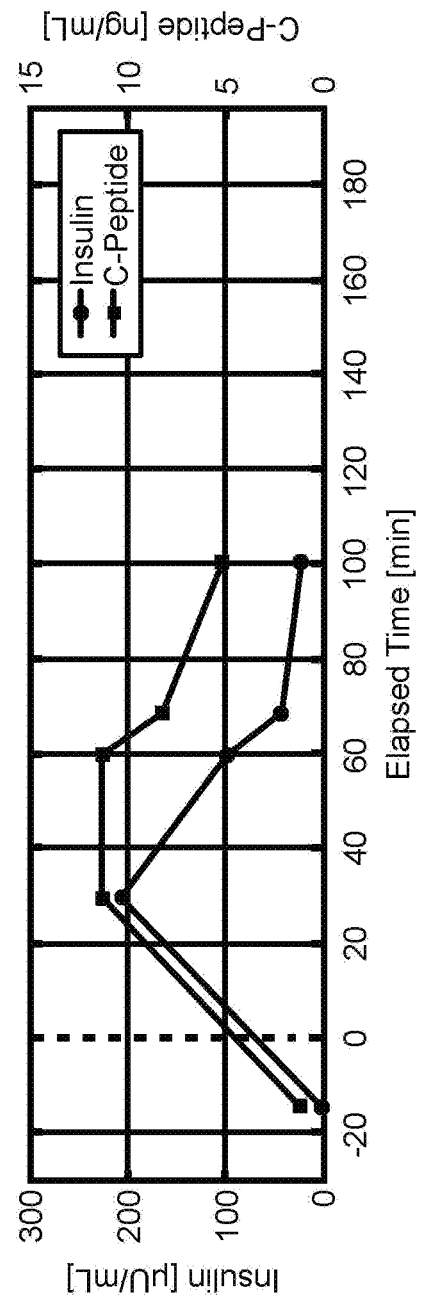
FIG. 9B shows an X-Y plot of time versus insulin concentration in the blood of a subject when a 300 μg glucagon dosage is injected according to an embodiment of the present disclosure.
Figure 10:
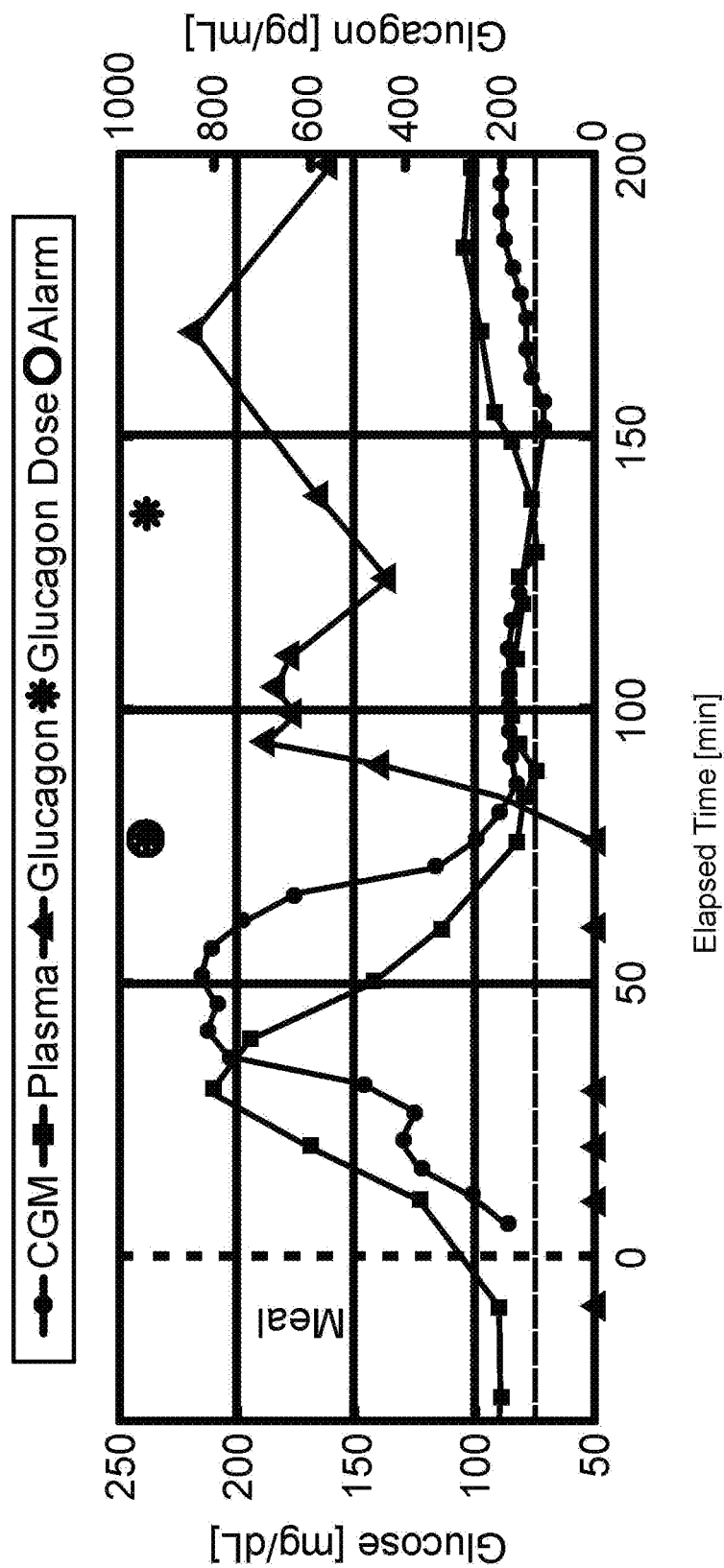
FIG. 10 shows an X-Y plot of time versus glucose concentration in the blood of a subject when two glucagon doses are injected according to an embodiment of the present disclosure.

Therefore, FIG. 6 shows a small variety of potential embodiments that the present disclosure can take. For example, HPA can vary according to its inclusion of one or both of LGP and PBH detection. HPA can give instructions for one or more glucagon dosages, and the dosage amounts can vary. For example, the dosage amounts can vary between 150 and 300 μg. The results of studies conducted to the exemplary stages A-D are discussed further with regards to FIGS. 7A-12D. Stage A data is depicted in FIGS. 7A and 7B. Stage B data is depicted in FIGS. 8A and 8B. Stage C data is depicted in FIGS. 9A and 9B. Stage D data is depicted in FIG. 10.

FIGS. 7A, 8A, 9A, and 10 show that, after a meal event, subjects' glucose levels typically rise and later fall again. Glucose levels can hit a lowest concentration around 100 minutes after the meal. The lowest concentration is typically below a hypoglycemic threshold. The CGM lines show a continuous glucose monitor which collects data on a subject's glucose levels and reports them to the HPA. The CGM lines closely follow the plasma glucose levels. This indicates that CGM provides a detailed overview of glucose levels in the subject. The alarm events shown depict when an alarm is sent by the system according to an exemplary impending hypoglycemia protocol. The star glucagon dose event shows when a glucagon dose is injected into the subject. The glucagon line represents the concentration of glucagon in a patient's bloodstream. The glucagon line is typically at or close to zero before the glucagon dose event. The subsequent rise in glucagon concentration after the glucagon dose event shows that the study, according to an embodiment of the present disclosure, is successful at injecting glucagon and causing a subsequent rise in blood glucagon levels to offset hypoglycemia.

FIGS. 7B, 8B, and 9B shows an X-Y plot of time versus insulin concentration in the blood of a subject during a Stage A, Stage B, and Stage C (respectively) study conducted according to an embodiment of the present disclosure. For example, before a meal, a subject's levels of Insulin and C-peptide are typically at 0. After a meal, both typically rise to a peak shortly before forty minutes, and then fall again.

FIG. 7A, in particular, shows an X-Y plot of time versus glucose concentration in the blood of a subject during a Stage A study conducted according to an embodiment of the present disclosure. FIG. 7A shows how a dose of insulin delivered close in time to when the subjects' glucose levels go below a hypoglycemic threshold can correspond to a subsequent rise in glucose levels. For example, the star represents a time when a glucose dose is given, shortly after 100 minutes. By approximately 140 minutes, the subjects' glucose levels have risen. However, the glucose levels do not rise significantly above a hypoglycemic threshold. This indicates that a dose of 150 µg may not be sufficient to offset hypoglycemia.

FIG. 7B shows an X-Y plot of time versus insulin concentration in the blood of a subject during a Stage A study conducted according to an embodiment of the present disclosure. The glucagon dose event, depicted in FIG. 7A, corresponds to a subsequent slowing of the decrease in insulin and C-peptide as shown in FIG. 7B. This shows the effectiveness of a glucagon dose to slow or prevent hypoglycemia.

FIG. 8A shows an X-Y plot of time versus glucose concentration in the blood of a subject during a Stage B study conducted according to an embodiment of the present disclosure. FIG. 8A shows how, similar to FIG. 7A, after a meal event, subject's glucose levels would typically rise and start falling again. FIG. 8A however, shows a glucagon dose which is given approximately 90 minutes after a meal event, and corresponds to shortly before the glucose levels fall below a hypoglycemic threshold. Thus, Stage B delivers a glucagon dose before Stage A. FIG. 8A shows that the earlier delivered glucagon dose allows a subsequent increase in the subjects' glucose levels which rises well above the hypoglycemic threshold, and even above a detection threshold.

FIG. 8B shows an X-Y plot of time versus insulin concentration in the blood of a subject during a Stage B study conducted according to an embodiment of the present disclosure. FIG. 8B shows the superiority of a LGP detection combined with a PBH detection because the insulin and C-peptide levels do not fall to zero as shown in FIG. 7B. Additionally, the decline in insulin and C-peptide is slower which can be attributed to the earlier glucagon dose.

FIG. 9A shows an X-Y plot of time versus glucose concentration in the blood of a subject during a Stage C study conducted according to an embodiment of the present disclosure. FIG. 9A shows a glucagon dose event close in time to an alarm event. Both are close in time to when the plasma and CGM levels fall below a hypoglycemic threshold. FIG. 9A shows how the LGP algorithm and the PBH algorithm can detect impending hypoglycemia and provide a glucagon dose which raises blood levels of glucose.

FIG. 9B shows an X-Y plot of time versus insulin concentration in the blood of a subject during a Stage C study conducted according to an embodiment of the present disclosure. FIG. 9B shows that, similarly to FIG. 8B, insulin and C-peptide levels do not fall to zero as shown in FIG. 7B. Additionally, the decline in insulin and C-peptide is slower in FIG. 9B than in FIG. 7B. This can be attributed to an earlier glucagon dose or the higher amount of the glucagon dose.

FIG. 10 shows an X-Y plot of time versus glucose concentration in the blood of a subject when two glucagon doses are injected according to an embodiment of the present disclosure. FIG. 10 shows a glucagon dose event close in time to an alarm event. Both are close in time to when the plasma and CGM levels fall below a hypoglycemic threshold. FIG. 10 also shows a second glucagon dose when the subject's blood glucose levels do not rise sufficiently above the hypoglycemic threshold. After the second glucagon dose, the plasma glucose levels and CGM rise above the hypoglycemic threshold and return to a safe level of 100 mg/dL. Therefore, FIG. 10 shows the effectiveness of a second glucagon dose where glucose levels have not returned to safe levels after a first glucagon dose.

Figure 11A:
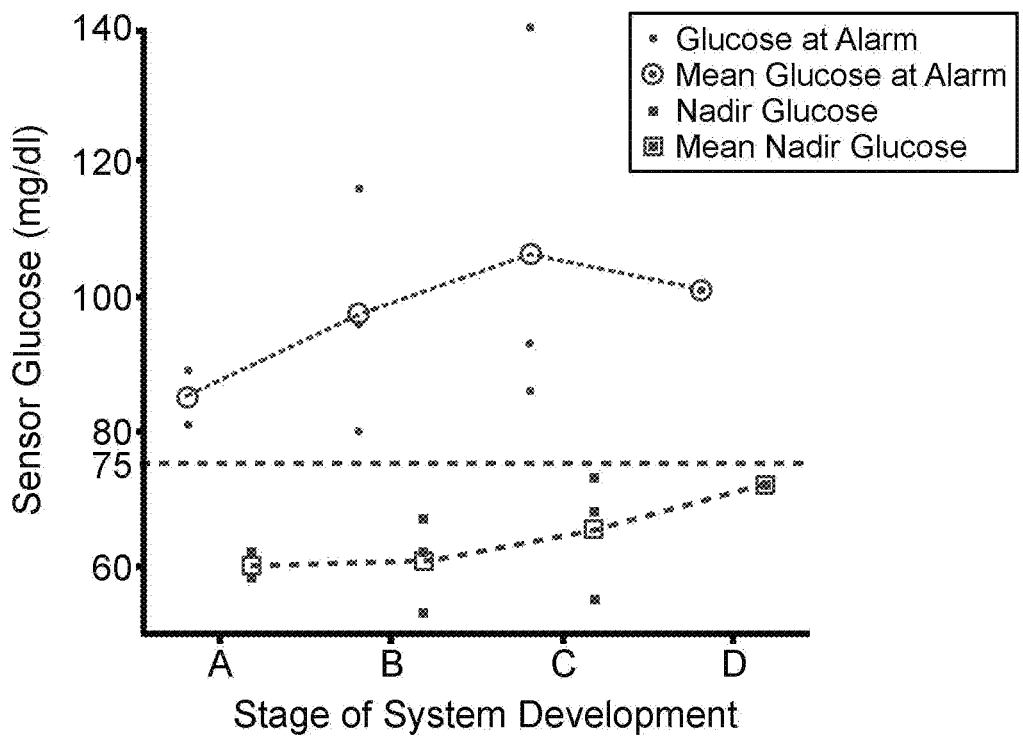
FIG. 11A shows a plot of sensor glucose between exemplary algorithm methodologies according to various embodiments of the present disclosure.

FIG. 11A shows a plot of sensor glucose between exemplary algorithm methodologies according to various embodiments of the present disclosure. FIG. 11A compares glucose levels as detected by a sensor across Stages A-D. FIG. 11A shows that Stages B-D have earlier alarms and thus the mean glucose at an alarm is higher than the alarm glucose level of Stage A. This shows that combined PBH and LGP detection provides earlier notice of impending hypoglycemia than just LGP detection. FIG. 11A also shows the mean Nadir glucose—or the lowest point on a blood glucose curve. A lower point corresponds to a more dangerous glucose level for the health of the subject. The mean nadir glucose is higher for Stages B-D which shows the superiority of a combined PBH and LGP detection.

Figure 11B:
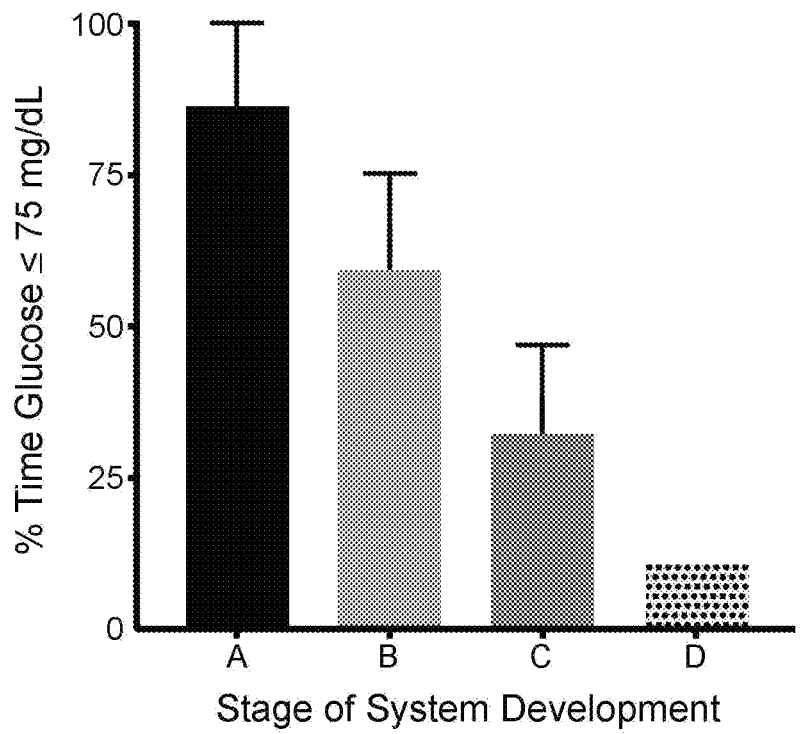
FIG. 11B shows a plot of the length of time that a subject's glucose concentration is below a hypoglycemic threshold according to various embodiments of the present disclosure.

FIG. 11B shows a plot of the length of time that a subject's glucose concentration is below a hypoglycemic threshold according to various embodiments of the present disclosure. FIG. 11B shows the superiority of the combined PBH and LGP detection in Stages B-D to the sole LGP detection in Stage A. Stage A has a longer percentage of time that the subject has a glucose concentration below a hypoglycemic threshold. This indicates greater danger to the physical health of the subject.

FIGS. 12A-12D show X-Y plots of hypoglycemic symptom scores over time during studies conducted according to embodiments of the present disclosure. FIGS. 12A-12D respectively show Stage A-D studies. The Edinburgh Hypoglycemia Scale was used to assess hypoglycemia symptoms at baseline, at the time of a hypoglycemia prediction alarm, and 15, 30, and 60 min after a glucagon dose. This scale includes 5 autonomic, 8 neuroglycopenic, 5 nonspecific, and 10 unrelated (dummy) symptoms. Scores for the 5 autonomic, 8 neuroglycopenic, and 5 nonspecific symptoms were summed for each time point. The scores are plotted as mean±SD. At the time of the predicted hypoglycemia alert, patients reported autonomic, neuroglycopenic and nonspecific symptoms, with numerically higher scores than a baseline score. Symptom scores remained 18% above baseline by 15 minutes after glucagon injection. By 30 and 60 minutes after glucagon injection, symptom scores decreased to or below baseline.

FIG. 12A has the greatest summation of symptom scores across the length of the study. This shows the superiority of Stages B-D in decreasing hypoglycemia symptoms. Stage D shows the lowest, continuous symptom scores which suggests the advantages of two separate glucagon dosages.

Figure 13:
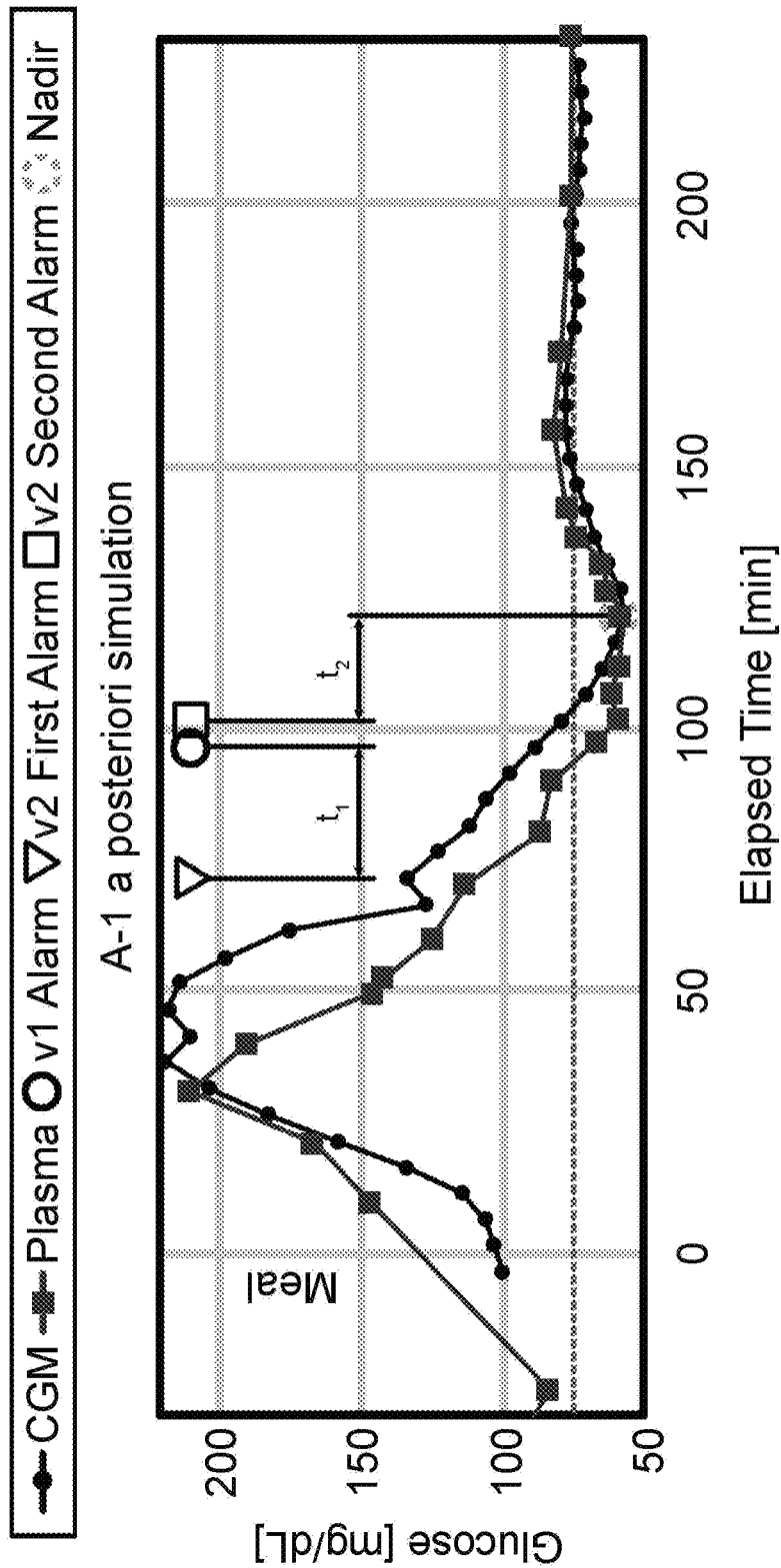
FIG. 13 shows an X-Y plot of glucose versus time to show an exemplary difference between timed alarms of various embodiments of the present disclosure.
Figure 15A:
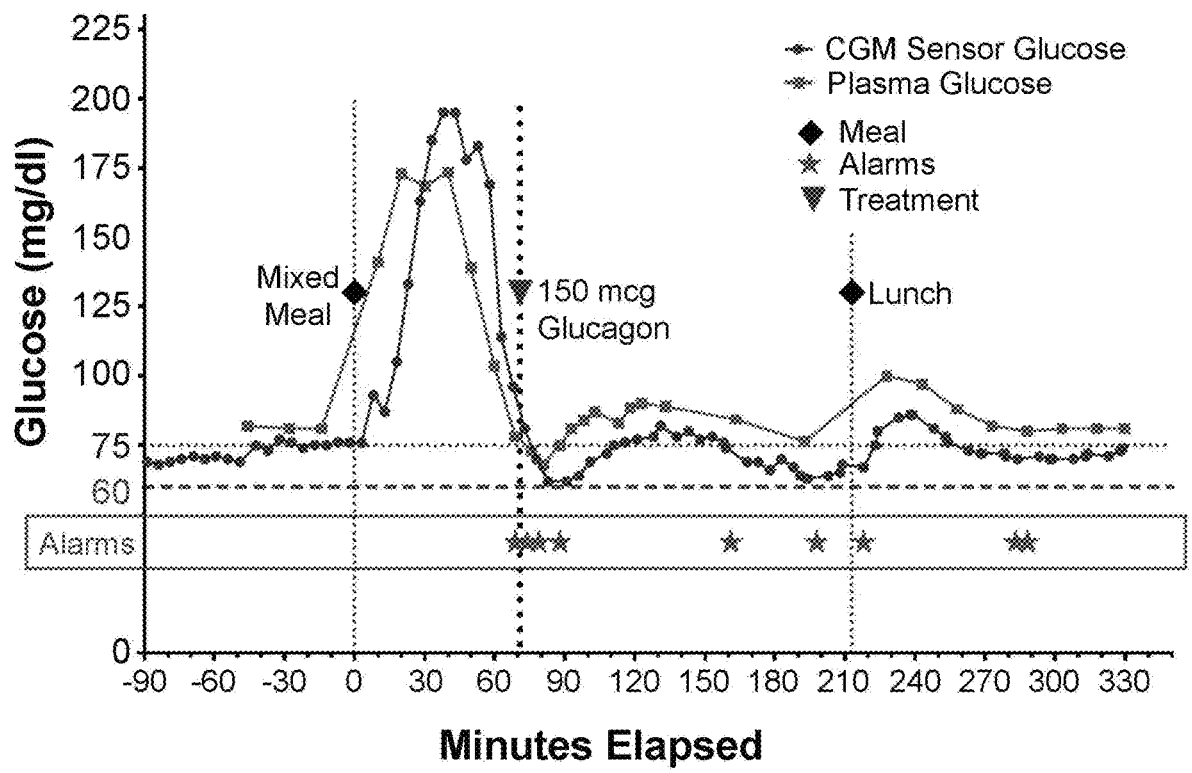
FIG. 15A shows an X-Y plot of glucose versus time for an exemplary glucagon injection methodology according to an embodiment of the present disclosure.

FIG. 13 shows an X-Y plot of glucose versus time t for a participant of a Stage A study, conducted according to an embodiment of the present disclosure. FIG. 15A is a posteriori simulation of data from the patient.

The circle represents the timing of a first alarm according to an embodiment of the present disclosure which relies on only LGP detection (a first version embodiment). The triangle represents the timing of a first alarm according to an embodiment of the present disclosure which relies on LGP and PBH detection (a second version embodiment). Therefore, a combined LGP and PBH detection results in earlier notification of impending hypoglycemia than just LGP detection. $T_1$ represents the length of time that a second version embodiment provides an earlier alarm as compared to a first version embodiment. Additionally, the combined LGP and PBH detection can provide a second alarm when glucose levels continue to fall. $T_2$ represents the length of time between the second alarm and a nadir glucose level.

Glucose Monitoring and Glucagon Injection System

FIG. 14 shows an exemplary glucose level monitoring and glucagon injection system 1400 according to an embodiment of the present disclosure. The system can include a subject 1402; a glucagon pump 1404; a biological sensor and transmitter 1406; a sensor data receiver 1408; a controller computer system 1410; a mobile device 1412; and a stable liquid glucagon 1414.

The subject 1402 can have a glucagon pump 1404 and a biological sensor and transmitter 1406 attached to the subject's body 1402. The glucagon pump 1404 can be an Omnipod pump or any other pump or on body delivery device filled with a stable liquid glucagon 1414. The glucagon pump 1404 can be equipped to inject the stable liquid glucagon 1414 into the subject's abdomen 1402 when instructed to do so via a wireless transmission from the controller computer system 1410.

The biological sensor and transmitter 1406 can be inserted into an anterior abdominal wall of the subject 1402. An exemplary biological sensor and transmitter 1406 can be a Dexcom G4 CGM, or any other sensor which can collect data on a subject's blood glucose and wirelessly transmit to a computer system. In the system 1400 depicted in FIG. 14, the Dexcom CGM wireless transmits glucose values to the controller computer system 1410. The biological sensor and transmitter 1406 can be calibrated with the subject's assistance to ensure accuracy of the measurements. For example, multiple biological sensors can be placed in a subject's abdomen and the sensor with the best calibration can be selected. The biological sensor and transmitter 1406 can be configured to measure sensor and plasma glucose, insulin, C-peptide, and glucagon concentrations. The biological sensor and transmitter 1406 can take measurements both at a baseline level when no food is in the stomach or no hypoglycemia is detected. The biological sensor and transmitter 1406 can continue to measure after a meal has been taken or a after the subject has received a glucagon dose.

The biological sensor and transmitter 1406 can be configured to wirelessly send glucose data to a sensor data receiver 1408. For example, the sensor data receiver 1408 can be a Dexcom receiver, or any other receiver configured to wirelessly receive sensor data from a biological sensor and transmitter 1406. The sensor data receiver 1408 can be configured to connect to the controller computer system 1410 by a wired connection. By this wired connection, the sensor data receiver 1408 can provide data on glucose levels from the biological sensor and transmitter 1406 to the controller computer system 140.

The controller computer system 1410 can be configured to receive sensor data from the biological sensor and transmitter 1406 and run the data through HPA to detect impending hypoglycemia, enact an impending hypoglycemia protocol, and command the glucagon pump 1404 to inject a shot of glucagon. The controller computer system 1410 can run a HPA in accordance with various embodiments of the present disclosure and discussed with respect to FIGS. 2A-4A and FIG. 5A. The controller computer system 1410 can enact an impending hypoglycemia protocol in accordance with the present disclosure, including enacting the protocol discussed with respect to FIG. 2B.

The controller computer system 1410 can also be configured to wirelessly send an alert to a mobile device 1412. The alert can be an audible alarm or a text message or any other method of notifying an owner of the mobile device. The alert can indicate that the blood glucose levels of the subject are approaching hypoglycemia. The alert can include a current glucose level, a current ROC, a predicted time when the blood glucose levels will fall below a hypoglycemic threshold, a length of time until the blood glucose levels fall below the hypoglycemic threshold, a predicted time when the blood glucose levels will reach a nadir, and/or a length of time until the blood glucose levels reach a nadir. In some embodiments, the alert can be sent to multiple mobile devices or other computer systems. The controller computer system 1410 can store the alerts and the data received from the biological sensor and transmitter 1406.

The stable liquid glucagon 1414 can be a stable liquid formation of native glucagon which can be delivered through an infusion pump 1404. The stable liquid glucagon 1414 allows lower 'minidoses' to be delivered when hypoglycemia is imminent. Additionally, a stable liquid glucagon eliminates the need for a patient to reconstitute glucagon powder and inject while the patient is about to experience hypoglycemia. Conventional glucagon reconstruction doses must be used within twenty-four hours and can cause nausea and hyperglycemia. By contrast, the stable liquid glucagon 1414, according to an embodiment of the present disclosure, provides a convenient, effective method of increasing a patient's glucose levels without nausea or hyperglycemia. Additionally, the stable liquid glucagon 1414 has a longer shelf-life than reconstituted glucagon. The stable liquid glucagon 1414 can be stored within the glucagon pump 1404.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example One. Clinical Trial Methodology

Participants with a history of RYGB surgery and neuroglycopenia, uncontrolled on medical nutrition therapy and medications, can be recruited. A clinical trial can exclude participants with the following exclusion criteria: fasting hypoglycemia, known insulinoma, major systemic illness, pregnancy, substance or alcohol abuse, recent steroid or investigational drug exposure, and use of medications (beyond hypoglycemia treatment) known to affect insulin secretion or action.

Four females and one male with PBH were enrolled, with average age (mean SD) of 47±7 years, current BMI 34 [27, 36] kg/m² (median [interquartile range]), hemoglobin $A_{1c}$ 5.6±0.2% and 90 [67, 131] months since RYGB surgery (Table 1).

TABLE 1

Participant Characteristics. Normally distributed data are expressed as mean ± SD; skewed data are expressed as median [interquartile range (IQR)].

| | |
|---|---|
| Gender [M:F] | 1:4 |
| Age [years] | 47 ± 7 |
| Time after RYGB surgery at study [months] | 90 [67, 131] |
| Time after RYGB to neuroglycopenia [months] | 25 [24, 55] |
| Preoperative BMI [kg/m²] | 42 [40, 49] |
| BMI at time of study [kg/m²] | 34 [27, 36] |
| Hemoglobin A1c [%] | 5.6 ± 0.2 |
| Received medical nutrition counseling | 100% |
| Regular use of anti-hypoglycemic medications | 60% |
| Comorbid conditions | |
| Depression | 80% |
| Nephrolithiasis | 60% |
| Obstructive Sleep Apnea | 60% |
| Hypertension | 60% |

All participants reported severe hypoglycemia with neuroglycopenia occurring between 12 and 150 months following surgery. All had received medical nutrition therapy[26] and 4 of 5 were on anti-hypoglycemic medications (e.g. acarbose, short-acting octreotide, diazoxide, and pramlintide, some in combination) at enrollment. None had a history of diabetes. Several participants had history of obesity-related comorbidities, including obstructive sleep apnea, hypertension and nephrolithiasis (each 60%) and depression (80%).

Initiation of glucagon delivery system and mixed meal tolerance testing. Two Dexcom® G4 Platinum CGM sensors were blinded and then inserted by study staff on the anterior abdominal wall. Participants were instructed to record food intake and capillary glucose prior to and two hours after each meal, and to perform CGM calibration when prompted. Participants were asked to return 48 to 72 hours later, after an overnight fast; medications, including alpha-glucosidase inhibitors, short-acting somatostatin analogues, and diazoxide, were held for at least 24 hours prior to the study visit. After placement of an intravenous catheter for blood sampling, a subcutaneous Omnipod pump filled with investigational glucagon (Xeris) was inserted on the anterior abdominal wall. After calibration of both CGM, the sensor with glucose values most closely matching the serum glucose measured in the study room by YSI was connected to the Windows tablet running the portable Artificial Pancreas System[27] (pAPS) and the PBH Detection Algorithm.

After baseline blood samples were drawn, a high-carbohydrate liquid mixed meal (two bottles of Ensure Compact, providing 64 g carbohydrate, 18 g protein, 236 ml volume) was consumed by the participants over 5 minutes. The high-carbohydrate liquid meal was chosen to provoke glycemic patterns typical for PBH, including hypoglycemia, in order to test the capacity of the semi-automated glucagon system to detect and respond to hypoglycemia. Sensor and plasma glucose (YSI), insulin, and glucagon were measured at baseline and at predetermined intervals for 2 hours following glucagon delivery.

When HPA predicted a hypoglycemic event, defined conservatively as glucose less than 75 mg/dL (to ensure safety during the study), an alert was generated in two ways: (1) an audible alarm was emitted from the pAPS device and (2) a text message (SMS) was sent to the study physicians and technical team. Upon receipt of the alert, a venous blood sample was obtained. The study physician then activated the Omnipod pump to deliver a single dose of investigational glucagon, 150 µg over 2.25 minutes, and the pump was removed 30 minutes after glucagon delivery. After two hours, a standard low carbohydrate lunch was provided, and participants were observed for two additional hours prior to discharge.

Glucose Measurements. Plasma glucose was measured by glucose oxidation (YSI 2300 STAT), and insulin by electrochemiluminescence (Roche Diagnostics, Celerion, Lincoln, NE). Using solid phase extraction, plasma glucagon was quantified with an LC-MS/MS instrument using weighted quadratic regression analysis of peak area ratios of the analyte and internal standard (Celerion, Lincoln, NE).

Investigational Glucagon Formulation. Glucagon[29] (Xeris Pharmaceuticals) was provided to the investigator in vials as a pre-mixed liquid stored at controlled room temperature. Before and after the study, vials were sampled and the solution was subjected to high-performance liquid chromatography (HPLC, Integrity Bio, Inc. Camarillo, CA) to determine the concentration of glucagon.

Hypoglycemia Prediction Algorithm. A PBH Detection System (PBH-DS) in can be implemented in a pAPS[27], a computer interface running in a Windows 7 tablet with WiFi connectivity. The software can be configured to (1) register and store all values from the CGM sensor, provide values to the PBH-DS, and (2) communicate impending hypoglycemia to the clinical team, via both auditory and text message alert indicting severity and prediction time. The PBH-DS is a hypoglycemia prediction algorithm designed specifically for patients with PBH. PBH-DS is composed of two modules working simultaneously to alert for impending hypoglycemia. The integration of the two modules offers redundancy to provide additional safety. The first alarm is the PBH alarm, which detects impending hypoglycemia up to 30 minutes before it occurs, after a meal has been consumed. A second module is the LGP alarm which detects impending hypoglycemia, even without preceding meal ingestion.

The combination of LGP alarms and PBH alarms allows for a much faster warning to the clinical team in the case of a rapid descent of glucose after a meal, while still maintaining the detection strengths of the original LGP algorithm. The algorithm implements a safety "lockout" mechanism that prevents issuing an alarm if a hypoglycemia alert had been issued recently (30 minutes, or 15 minutes if glucose <60 mg/dL).

Numerical values for relevant metrics are provided in Table 2, which includes prediction alarms, glucose, glucagon, insulin, and time intervals during the mixed meal tolerance test. <LLOQ: Below low limit of quantification (<100 pg/mL for glucagon assay). Normally distributed data are expressed as mean±SD; skewed data are expressed as median and interquartile range. The participants are arranged in the order that the study was performed.

TABLE 2

| Time | Metric | | Participant | | | | | Mean (Median) | SD [Interquartile Range] |
|---|---|---|---|---|---|---|---|---|---|
| | | | #1 | #2 | #3 | #4 | #5 | | |
| Time 0 (fasting) | Glucose [mg/dL] | sensor | 97 | 73 | 75 | 72 | 83 | 80 | 10 |
| | | plasma | 83 | 82 | 81 | 83 | 94 | 85 | 5 |
| | Glucagon [pg/ml] | | <LLOO | <LLOO | <LLOO | 127 | <LLOO | [0] | [0, 64] |
| | Insulin [µU/ml] | | 0 | 0 | 3 | 7 | 5 | 3 | 3 |
| After mixed meal | Peak glucose [mg/dL] | sensor | 218 | 197 | 195 | 240 | 180 | 206 | 23 |
| | | plasma | 209 | 195 | 174 | 232 | 216 | 205 | 22 |
| | Peak insulin [µU/ml] | | 253 | 221 | 206 | 243 | 247 | 234 | 20 |
| | Peak glucagon [pg/ml] | | 106 | <LLOO | <LLOO | <LLOO | <LLOO | <LLOO | — |
| | Maximum glucose ROC [mg/dL/min] | sensor | 5 | 11 | 6 | 13 | 4 | 8 | 4 |
| | Minimum glucose ROC [mg/dL/min] | sensor | −10 | −9 | −11 | −2 | −9 | [−9.3] | [−10, −6] |
| | False alarms before glucagon | | 0 | 1 | 0 | 0 | 0 | [0] | [0, 0.5] |
| Hypoglycemia prediction alarm | Glucose [mg/dL] | sensor | 89 | 81 | 96 | 80 | 116 | 92 | 15 |
| | | plasma | 68 | 71 | 78 | 81 | 91 | 78 | 9 |
| | Delta sensor & plasma glucose [mg/dl] | | 21 | 10 | 18 | −1 | 25 | 15 | 10 |
| | Glucagon [pg/ml] | | <LLO | <LLO | <LLO | <LLO | <LLO | <LLOO | — |
| | Insulin [µU/ml] | | 18 | 13 | 43 | 3 | 76 | 31 | 30 |
| | Time to alarm [min] | | 96 | 122 | 69 | 164 | 73 | 105 | 39 |
| | Alarm to glucagon delivery [min] | | 11 | 7 | 2 | 4 | 5 | 6 | 3 |
| After glucagon bolus | Nadir glucose [mg/dL] | sensor | 58 | 62 | 62 | 53 | 67 | 60 | 1 |
| | | plasma | 57 | 49 | 68 | 60 | 59 | 59 | 7 |
| | Peak glucagon [pg/mL] | | 484 | 319 | 520 | 436 | 175 | 387 | 141 |
| | Insulin 30 minutes after glucagon [µU/ml] | | 6 | 7 | 22 | 9 | 63 | [9] | [6, 42] |

Mean fasting plasma glucose was 85±5 mg/dL, with corresponding insulin of 3±3 µU/mL, consistent with appropriate suppression of insulin in the fasting state in PBH. There was no hypoglycemia reported by any of the participants during the night prior to the mixed meal tolerance test. One participant had a detectable baseline glucagon (127 pg/mL); all others were below the lower limit of quantification for the assay (<100 pg/mL). After the liquid meal challenge, all participants had a rapid rise in sensor glucose (maximum positive rate of change 8±4 mg/dL/min), reaching a mean peak plasma glucose of 205±22 mg/dL. Subsequently, sensor glucose rapidly declined, at a median rate of change of −9.3 [−10, −6] mg/dL/min. The predictive hypoglycemia alert was triggered at a mean of 105±39 minutes after the meal, prompting physician delivery of 150 µg of glucagon via pump. Participant 2 presented a false hypoglycemia alarm shortly after meal ingestion. This alarm was disregarded by the clinicians since it was deemed that meal dynamics could not have triggered such an early hypoglycemic event.

HPA successfully generated alerts before reaching the hypoglycemia threshold in the first two participants, at sensor and plasma values of 89 and 68 mg/dL, respectively, for participant 1, and 81 and 71 mg/dL for participant 2. However, plasma glucose values for the first two participants were already below the plasma threshold of 75 mg/dL at the time of the alarm. Despite glucagon administration, subsequent nadir glucose was 58 and 62 for the CGM sensor and 57 and 49 for plasma values.

Sensor-based detection of glycemia is known to lag behind plasma levels of glucose[35]; this pattern is exacerbated when glucose levels are rapidly changing, as in the postprandial state in patients with PBH. Indeed, sensor glucose was 21 and 10 mg/dL greater than plasma levels at the time of the alarm in participants 1 and 2, respectively.

Given the rapid declines in glucose in the postprandial state observed in the first two participants (up to −11 mg/dL/min) and the sensor lag, the embodiments of the present disclosure allow for earlier prediction of hypoglycemia. Meal-related glucose excursions and peaks can be identified, and then trigger implementation of the PBH-specific algorithm at a higher glucose threshold (i.e. when sensor glucose values were less than 150 mg/dL), using an extended prediction window (30 minutes), and limiting rate of change to 5 mg/dL. Such an exemplary algorithm is capable of issuing alerts (the PBH alarm) earlier, as demonstrated by in silico testing showing that alarms would have happened 25 and 39 minutes earlier, respectively, than the initial algorithm for participants 1 and 2, thus allowing the team to deliver glucagon at an earlier time point. This modified system was implemented for clinical studies for participants 3-5.

Using the modified algorithm, sensor (78, 81, 91) and plasma (96, 80, 116) glucose levels for the next three participants were higher at the time of alert than those of the first two participants. Moreover, nadir plasma glucose levels were increased in the last three participants to 68, 60 and 59 mg/dL versus 57 and 49 mg/dL for participants 1 and 2. The fourth participant required oral glucose (16 grams) for neuroglycopenia at 88 minutes after the glucagon bolus, while the fifth participant required oral glucose at 15 minutes (16 grams) and 90 minutes (10 grams) after glucagon. No rebound hyperglycemia was observed in any participant.

Adverse events. Three participants described varying degrees of discomfort at the site of glucagon infusion which lasted for the duration of infusion (about two minutes). The infusion site was examined at 30 and 60 minutes following glucagon administration by the study physician and then again by the participant 24 hours later. At 30 minutes, erythema was well-defined in one participant, moderate in two, and barely perceptible in the other two; barely perceptible edema was noted in a single participant. Moderate erythema persisted in two individuals by 60 minutes, while decreasing to barely perceptible in two participants. At 24 hours after the meal test all participants reported complete resolution of any skin changes at the infusion site. No participant had systemic rash or nausea, and there were no serious adverse events.

Hormonal evaluation. There was a robust increase in insulin levels after meal ingestion as previously described in patients with PBH[9,10], with peak insulin levels of 234±20 μU/mL at 30 minutes following mixed meal. At the time of the hypoglycemia alert, insulin levels had decreased to 31±30 μU/mL. Thirty minutes post-glucagon infusion, the median insulin level was 9 [6, 42] μU/mL. In contrast to prior studies demonstrating increased meal-stimulated glucagon levels in post-bypass patients, both with and without neuroglycopenia[9,10], post-meal glucagon levels remained below assay detection limit in all but 1 participant in the current study. Glucagon levels were undetectable at the time of the predicted hypoglycemia alert, suggesting either impaired counterregulatory response[36] and/or inadequate duration of hypoglycemia for these responses. In response to glucagon infusion, peak glucagon levels achieved were 387±141 pg/mL. These values are similar to those achieved in prior mini-dose glucagon studies[25,37,38]

Post-study, HPLC analysis of the glucagon stock determined that the fixed injection volume of 30 μL used in the study provided approximately 110±5 μg of glucagon.

Study Results: For the first two participants, the alarm was triggered too late to achieve our primary endpoint, namely prevention of plasma glucose below 75 mg/dL. A subsequent modification of the prediction algorithm led to earlier alarms and maintained specificity, and translated into improved prediction power in the last three participants; none of the last three participants' plasma glucose was below the threshold at the time of the alarm. Glucagon bolus through the infusion pump was followed by an acute rise in serum glucagon levels and reversal of declines in glucose levels. Only two of five participants required rescue oral glucose.

Severe hypoglycemia in PBH often occurs after a high-carbohydrate mixed meal. While a central goal of medical nutrition therapy is reduced consumption of simple carbohydrates[26], a high-carbohydrate provocative test meal can be used in order to mimic conditions contributing to severe hypoglycemia. In these conditions, low nadir glucose and/or incomplete reversal of postprandial declines in glucose, despite glucagon infusion, may have resulted from several factors. First, insulin levels following mixed meal ingestion were very high, contributing to very rapid declines in glucose in the later postprandial state (up to −11 mg/dL/min). Such high insulin levels cannot be fully cleared within the timeframe of the postprandial absorption period, leading to an imbalance between glycemia and residual high insulin concentrations. Moreover, insulin signal transduction in insulin-responsive tissues continues long after plasma insulin levels have decreased, contributing to sustained hypoglycemic effects. Second, the required human response to the automatically-generated alarm resulted in a delay in delivery of the glucagon bolus. While the delay was reduced after optimization of the protocol, closed-loop systems may be more effective to overcome this delay. Third, the mini-dose of glucagon (150 μg) selected for this study is substantially smaller than standard emergency rescue doses used for hypoglycemia rescue kits (1 mg), and may not be sufficient in the setting of high ambient plasma insulin concentrations and/or sustained tissue insulin action in PBH. Since this was the first implementation of the Xeris glucagon formulation in mini-doses in PBH, the dosage required to effectively prevent hypoglycemic events in the postprandial setting will likely be higher than that administered in the current study. Only one dose was permitted in the current study, and repeat dosing may be required in follow up studies. Finally, the doses of glucagon delivered, which were based on giving a fixed volume from stocks of glucagon for which concentration had been previously determined by HPLC analysis, were actually on average 25% lower than the targeted value of 150 μg due to both analytical technique and expected losses due to drug degradation. No participant received higher dosing than targeted.

Example Two: Clinical Trial Data

FIG. 15A shows an X-Y plot of glucose versus time for an exemplary glucagon injection methodology according to an embodiment of the present disclosure. As seen in FIG. 15A, alarm events are depicted as starts. Alarm events occur every time the HPA indicates that predicted glucose levels fall below a hypoglycemic threshold. A treatment event is shown as the triangle symbol at seventy minutes, where the patient's glucose levels fall below the hypoglycemic threshold of 75 mg/dL. FIG. 15A shows that the glucagon dose helped the plasma glucose levels to rise above the hypoglycemic threshold and largely stay above the threshold until a lunch event at approximately 210 minutes.

Figure 15B:
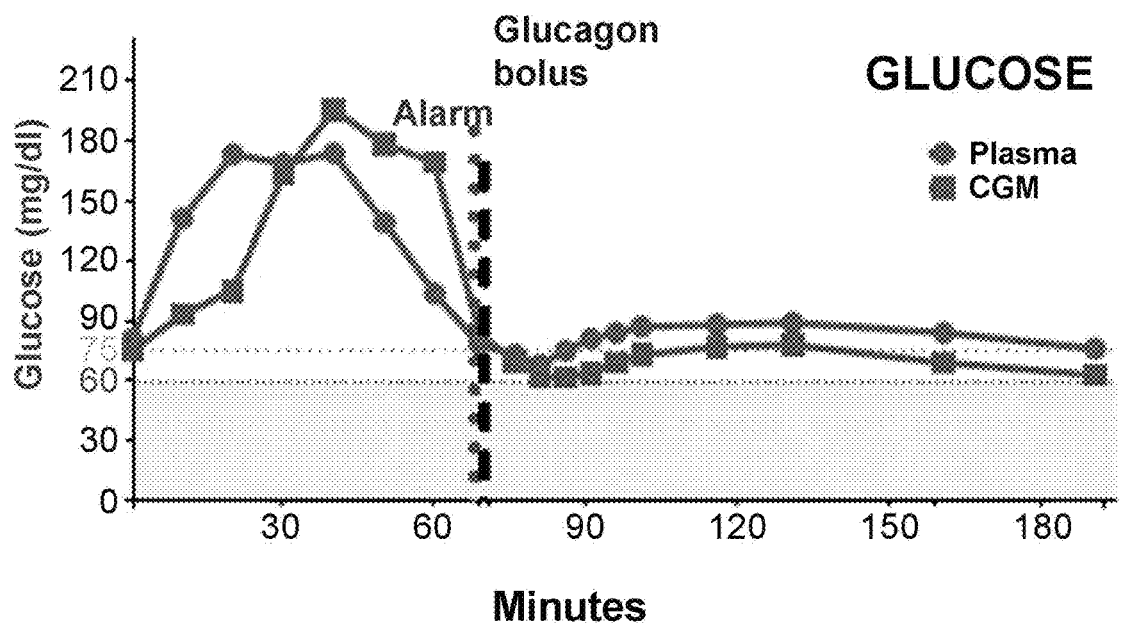
FIG. 15B shows a smoothed X-Y plot of glucose versus time for an exemplary glucagon injection methodology according to an embodiment of the present disclosure.

FIG. 15B shows a smoothed X-Y plot of glucose versus time for an exemplary glucagon injection methodology according to an embodiment of the present disclosure. Any data can be smoothed according to an embodiment of the present disclosure by using a four-sample moving-average filter which creates a series of averages of different subsets of the full data set. FIG. 15B shows that glucose levels generally rise and stay above a hypoglycemic level of 60 mg/dL after a glucagon dose is given.

Example Three: Algorithm Modes and Transitions Between Modes

Glycemic patterns following a mixed-meal are characterized by an initial postprandial peak, followed by a very rapid drop in glucose (high negative ROC). This very rapid drop in glucose provides little time for the PBH-DS to react (issue an alert) before hypoglycemia occurs. These patterns inspired the design of a meal detection routine (described below) that would change the algorithm mode if a meal had been recently detected. The routine, which is called after every sensor glucose sample, works by analyzing CGM history (up to two hours of data) and the current ROC. Given the noisy nature of the ROC of the CGM samples, a smoothed version of the ROC ($ROC_F$) can be calculated using a four samples moving average filter. The algorithm switches between three modes of operation which can include "waiting for meal," "waiting for peak", and "waiting for hypoglycemia."

"Waiting for meal" is the system's default state. If the three most recent estimated $ROC_F$ were greater than 1 mg/dL/min, the system assumes a meal has been consumed and switches the state to "waiting for peak."

"Waiting for peak." This state waits for the ROC sign to change. When $ROC_F$<0, the postprandial glycemic peak is detected, and the algorithm registers the time ($t_{PEAK}$). The average $ROC_F$ ($G'_{MEAL+}$) of the CGM signal in the past 45 minutes is also registered, as an estimation of the rate of ascent of the detected meal.

The system can switch its mode of operation to "waiting for hypoglycemia" when a meal peak is detected. In this state the system observes the CGM trend using just an LGP algorithm, until a hypoglycemia event is detected or two hours have passed from $t_{PEAK}$.

Example Four: Generating Alerts

Calculating Time to Hypoglycemia: An estimation of the potential time to hypoglycemia is then calculated:

$$HTime_{MEAL} = t_{PEAK} + \frac{G_F(t_{PEAK}) - th}{G'_{MEAL+}} \quad (1)$$

where $HTime_{MEAL}$ is the estimated time of hypoglycemia for the current meal. $HTime_{MEAL}$ is not intended to be an accurate representation of the actual PBH alarm time, but rather a limit of operation of the PBH alarm, i.e. PBH alarms are expected to happen before $HTime_{MEAL}$.

The following parameters can be used: $\Delta G=5$ mg/dL/min is the maximum allowed difference between consecutive CGM samples by the noise-spike filtering module, $\tau_F=3$ min is the time constant of the low-pass filter, #al=1 is the number of consecutive alarms necessary to issue a hypoglycemia alert, th=75 mg/dL is the hypoglycemic threshold, ph=30 min is the prediction horizon for hypoglycemia, $G_{MAX}=150$ mg/dL is the glucose threshold beyond which the algorithm will not issue PBH alarms, and $G'_{MAX}$ (−0.5 mg/dL/min) and $G'_{MIN}$(−5 mg/dL/min) are the maximum and minimum values of the glucose ROC for the detection algorithm to be active. The choice of these values for the parameters allows PBH alarms to be triggered faster than a solo LGP algorithm.

PBH alert: The following condition can be a requirement for a PBH alert to be issued:

$$t_{low}+t(k) \leq HTime_{MEAL}+hypo_w \quad (2)$$

where $hypo_w=10$ min is a new user-defined parameter. If the condition is satisfied, a PBH alert can be generated, but satisfaction of the condition does guarantee the alarm. $T_{low}$ (estimated time for glucose to violate the hypoglycemic threshold th) also needs to be lower than the prediction horizon ph. This new condition guarantees that the PBH alert will be triggered when glucose is rapidly decreasing after a meal. For slowly dropping postprandial glucose profiles, there is less necessity of early detection of hypoglycemia, and the detection relies on the LGP detection alert.

LGP alert: The LGP alert can be based on an optimized set of parameters. In contrast to the PBH alert, the LGP alert is called every sample, and does not require for the HPA to be in a particular state. One embodiment of the LGP parameters can be: $\Delta G=3$ mg/dL/min, $\tau_F=3$ min, #al=1, th=75 mg/dL, ph=15 min, $G_{MAX}=100$ mg/dL, $G'_{MAX}=-0.5$ mg/dL/min and $G'_{MIN}=-3$ mg/dL/min. A second embodiment of the LGP parameters can be: $\Delta G=5$ mg/dL/min, #al=2, ph=20 min and $G'_{MIN}=-5$ mg/dL/min. $\Delta G$ can be increased to relax the noise-spike filter against the fast-changing glucose profiles of PBH patients. Similarly, the second embodiment's $G'_{MIN}$ setting allows for much rapidly dropping glucose profiles to trigger alarms. #al's increase can avoid false alarms caused by the noisy nature of CGM sensors.

REFERENCES

1 Mingrone G, Panunzi S, De Gaetano A, et al. Bariatric-metabolic surgery versus conventional medical treatment in obese patients with type 2 diabetes: 5 year follow-up of an open-label, single-centre, randomised controlled trial. *The Lancet* 2015; 386: 964-73.
2 Schauer P R, Bhatt D L, Kirwan J P, et al. Bariatric Surgery versus Intensive Medical Therapy for Diabetes—3-Year Outcomes. *N Engl J Med* 2014; 370: 2002-13.
3 Halperin F, Ding S-A, Simonson D C, et al. Roux-en-Y Gastric Bypass Surgery or Lifestyle With Intensive Medical Management in Patients With Type 2 Diabetes: Feasibility and 1-Year Results of a Randomized Clinical Trial. *JAMA Surg* 2014; 149: 716-26.
4 Goldfine A B, Patti M E. How common is hypoglycemia after gastric bypass? *Obesity* 2016; 24: 1210-1.
5 Kefurt R, Langer F B, Schindler K, Shakeri-Leidenmühler S, Ludvik B, Prager G. Hypoglycemia after Roux-En-Y gastric bypass: detection rates of continuous glucose monitoring (CGM) versus mixed meal test. *Surg Obes Relat Dis* 2015; 11: 564-9.
6 Patti M-E, Goldfine A. Hypoglycemia after Gastric Bypass: The Dark Side of GLP-1. *Gastroenterology* 2014; 146: 605-8.
7 Sarwar H, Chapman W H, Pender J R, et al. Hypoglycemia after Roux-en-Y gastric bypass: the BOLD experience. *Obes Surg* 2014; 24: 1120-4.
8 Patti M E, Li P, Goldfine A B. Insulin response to oral stimuli and glucose effectiveness increased in neuroglycopenia following gastric bypass. *Obesity* 2015; 23: 798-807.
9 Salehi M, Gastaldelli A, D'Alessio D A. Altered Islet Function and Insulin Clearance Cause Hyperinsulinemia in Gastric Bypass Patients With Symptoms of Postprandial Hypoglycemia. *J Clin Endocrinol Metab* 2014; 99: 2008-17.
10 Goldfine A B, Mun E C, Devine E, et al. Patients with Neuroglycopenia after Gastric Bypass Surgery Have Exaggerated Incretin and Insulin Secretory Responses to a Mixed Meal. *J Clin Endocrinol Metab* 2007; 92: 4678-85.
11 Salehi M, Gastaldelli A, D'Alessio D A. Blockade of Glucagon-like Peptide 1 Receptor Corrects Postprandial Hypoglycemia After Gastric Bypass. *Gastroenterology* 2014; 146: 669-680.e2.
12 Craig C M, Liu L-F, Deacon C F, Holst J J, McLaughlin TL. Critical role for GLP-1 in symptomatic post-bariatric hypoglycaemia. *Diabetologia* 2017; 60: 531-40.
13 Kellogg T A, Bantle J P, Leslie D B, et al. Postgastric bypass hyperinsulinemic hypoglycemia syndrome: characterization and response to a modified diet. *Surg Obes Relat Dis* 2008; 4: 492-9.
14 Valderas J P, Ahuad J, Rubio L, Escalona M, Pollak F, Maiz A. Acarbose Improves Hypoglycaemia Following Gastric Bypass Surgery Without Increasing Glucagon-Like Peptide 1 Levels. *Obes Surg* 2012; 22: 582-6.
15 Moreira R O, Moreira R B M, Machado N A M, Gongalves T B, Coutinho W F. Post-prandial Hypoglycemia after Bariatric Surgery: Pharmacological Treatment with Verapamil and Acarbose. *Obes Surg* 2008; 18: 1618-21.
16 Myint K S, Greenfield J R, Farooqi I S, Henning E, Holst J J, Finer N. Prolonged successful therapy for hyperinsulinaemic hypoglycaemia after gastric bypass: the pathophysiological role of GLP1 and its response to a somatostatin analogue. *Eur J Endocrinol* 2012; 166: 951-5.
17 Gonzalez-Gonzalez A, Delgado M, Fraga-Fuentes M D. Use of diazoxide in management of severe postprandial hypoglycemia in patient after Roux-en-Y gastric bypass. *Surg Obes Relat Dis* 2013; 9: e18-9.
18 Fernindez-Esparrach G, Lautz D B, Thompson C C. Peroral endoscopic anastomotic reduction improves intractable dumping syndrome in Roux-en-Y gastric bypass patients. *Surg Obes Relat Dis* 2010; 6: 36-40.
19 McLaughlin T, Peck M, Holst J, Deacon C. Reversible Hyperinsulinemic Hypoglycemia after Gastric Bypass: A Consequence of Altered Nutrient Delivery. *J Clin Endocrinol Metab* 2010; 95: 1851-5.
20 Pernar L I M, Kim J J, Shikora S A. Gastric bypass reversal: a 7-year experience. *Surg Obes Relat Dis* 2016; 12: 1492-8.
21 Halperin F, Patti M E, Skow M, Bajwa M, Goldfine A B. Continuous glucose monitoring for evaluation of glycemic excursions after gastric bypass. *J Obes* 2011; 2011.
22 Clark A L, Best C J, Fisher S J. Even Silent Hypoglycemia Induces Cardiac Arrhythmias. *Diabetes* 2014; 63: 1457-9.
23 Vukmir R B, Paris P M, Yealy D M. Glucagon: Prehospital therapy for hypoglycemia. *Ann Emerg Med* 1991; 20: 375-9.
24 Halperin F, Patti M E, Goldfine A B. Glucagon Treatment for Post-Gastric Bypass Hypoglycemia. *Obesity* 2010; 18: 1858-60.
25 Castle J R, Youssef J E, Branigan D, et al. Comparative Pharmacokinetic/Pharmacodynamic Study of Liquid Stable Glucagon Versus Lyophilized Glucagon in Type 1 Diabetes Subjects. *J Diabetes Sci Technol* 2016; 10: 1101-7.
26 Suhl E, Anderson-Haynes S-E, Mulla C, Patti M-E. Medical nutrition therapy for post-bariatric hypoglycemia: practical insights. *Surg Obes Relat Dis* 2017; Online. DOI:10.1016/j.soard.2017.01.025.
27 Dassau E, Zisser H, C. Palerm C, A. Buckingham B, Jovanovič L, Doyle III F J. Modular Artificial 3-Cell System: A Prototype for Clinical Research. *J Diabetes Sci Technol Online* 2008; 2: 863-72.
28 Harvey R A, Dassau E, Zisser H, Seborg D E, Jovanovič L, Doyle III F J. Design of the Health Monitoring System for the Artificial Pancreas: Low Glucose Prediction Module. *J Diabetes Sci Technol* 2012; 6: 1345-54.
29 Newswanger B, Ammons S, Phadnis N, et al. Development of a Highly Stable, Nonaqueous Glucagon Formulation for Delivery via Infusion Pump Systems. *J Diabetes Sci Technol* 2015; 9: 24-33.
30 Hepburn D A, Deary I J, Frier B M, Patrick A W, Quinn J D, Fisher B M. Symptoms of Acute Insulin-Induced Hypoglycemia in Humans With and Without IDDM: Factor-Analysis Approach. *Diabetes Care* 1991; 14: 949-57.
31 Zisser H, Dassau E, Lee J, Bevier W, Doyle III F J. Clinical Results of an Automated Artificial Pancreas Using Technosphere Inhaled Insulin to Mimic First-Phase Insulin Secretion. *J Diabetes Sci Technol* 2015; 9: 564-72.
32 Dassau E, Brown S A, Basu A, et al. Adjustment of Open-Loop Settings to Improve Closed-Loop Results in Type 1 Diabetes: A Multicenter Randomized Trial. *J Clin Endocrinol Metab* 2015; 100: 3878-86.
33 Harvey R A, Dassau E, Bevier W C, et al. Clinical Evaluation of an Automated Artificial Pancreas Using Zone-Model Predictive Control and Health Monitoring System. *Diabetes Technol Ther* 2014; 16: 348-57.
34 Shapiro S S, Wilk M B. An analysis of variance test for normality (complete samples). *Biometrika* 1965; 52: 591-611.
35 Schmelzeisen-Redeker G, Schoemaker M, Kirchsteiger H, Freckmann G, Heinemann L, del Re L. Time Delay of CGM Sensors: Relevance, Causes, and Countermeasures. *J Diabetes Sci Technol* 2015; 9: 1006-15.
36 Abrahamsson N, Borjesson J L, Sundbom M, Wiklund U, Karlsson F A, Eriksson J W. Gastric Bypass Reduces Symptoms and Hormonal Responses in Hypoglycemia. *Diabetes* 2016; 65: 2667-75.
37 Ranjan A, Schmidt S, Madsbad S, Holst J J, Norgaard K. Effects of subcutaneous, low-dose glucagon on insulin-induced mild hypoglycaemia in patients with insulin pump treated type 1 diabetes. *Diabetes Obes Metab* 2016; 18: 410-8.
38 Haymond M W, Redondo M J, McKay S, et al. Non-aqueous, Mini-Dose Glucagon for Treatment of Mild Hypoglycemia in Adults With Type 1 Diabetes: A Dose-Seeking Study. *Diabetes Care* 2016; 39: 465-8.

Computer Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system for outputting an indication of an optimal time to deliver a dose of glucagon, the system comprising:
   a glucose sensor configured to output glucose data related to a concentration of glucose in the bloodstream of a patient;
   a glucagon pump;
   a memory containing machine-readable medium comprising machine executable code having stored thereon instructions for performing a method of delivering glucagon; and
   a control system coupled to the memory comprising one or more processors, the control system configured to execute the machine executable code to cause the processor to:
      store, in the memory, a model for determining an optimal time to inject glucagon based on a predicted blood glucose level;
      receive, from the glucose sensor, a set of glucose data;
      process the set of glucose data using the model to determine an optimal time to administer glucagon to the patient wherein the model comprises:
         a post-prandial hypoglycemia prediction module, designed to predict low glucose levels and identify when the patient's glucose level has fallen below a hypoglycemic threshold, upon at least a portion of the set of glucose data determined to be a meal pattern; wherein the meal pattern is determined by a positive rate of change (ROC) of the patient's glucose level followed by a negative ROC of the patient's glucose level; and a proximity hypoglycemia prediction module, designed to predict low glucose levels and identify whether a rising or falling ROC of the patient's glucose level indicates onset of post-bariatric hypoglycemia at a predetermined future time, upon at least the portion of the set of glucose data determined to be a non-meal pattern; and send a command to the glucagon pump to administer glucagon at the optimal time; and wherein the post-prandial hypoglycemia prediction module predicts low glucose levels and identifies when the patient's glucose level has fallen below a hypoglycemic threshold according to the following algorithms:
(a) if the glucose level is ≥100 mg/dL, then the glucose sensor continues to collect glucose data;
(b) if the glucose level is ≥75 mg/dL and <100 mg/dL, then the ROC of the glucose level is determined,
  (i) if the ROC is between −0.5 mg/dL/min and −5 mg/dL/min, then a time-to-hypoglycemia (TH) is determined based on the ROC,
    (A) if the TH is <20 minutes, then the patient's glucose level is predicted to fall below the hypoglycemic threshold, and the module generates an alert, takes a blood sample, and sends a command to inject glucagon: or
    (B) if the TH is not <20 minutes, then the glucose sensor continues to collect glucose data; or
  (ii) if the ROC is not between −0.5 mg/dL/min and −5 mg/dL/min, then the glucose sensor continues to collect glucose data; and
(c) if the glucose level is <75 mg/dL, then the ROC of the glucose level is determined,
  (iii) if the ROC is <−0.1 mg/dL/min, then the patient's glucose level is predicted to fall below the hypoglycemic threshold, and the module generates an alert, takes a blood sample, and sends a command to inject glucagon; or
  (iv) if the ROC is not <−0.1 mg/dL/min, then the glucose sensor continues to collect glucose data.

2. The system of claim 1, wherein the processor is further caused to determine whether the predicted blood glucose level will fall below a threshold within a window of time based on the model.

3. The system of claim 2, wherein the processor is further caused to determine the window of time based on the time of a subset of the set of glucose data that indicates the patient has recently consumed a meal.

4. The system of claim 1, wherein the proximity hypoglycemia prediction module is designed to predict when glucose level is below the predefined hypoglycemic threshold.

5. The system of claim 1, wherein the predetermined future time is less than thirty minutes.

6. The system of claim 1, wherein the patient has post-bariatric hypoglycemia.

7. The system of claim 1, wherein the onset of post-bariatric hypoglycemia occurs one to three hours after a meal.

8. The system of claim 1, wherein the positive ROC is at least 1 g/dL/min, and the negative ROC is less than 0 g/dL/min.

9. The system of claim 1, wherein the negative ROC is between −0.5 g/dL/min and −5.0 g/dL/min.

10. The system of claim 1, wherein the proximity hypoglycemia prediction module predicts low glucose levels and identifies whether a rising or falling ROC of the patient's glucose level indicates onset of post-bariatric hypoglycemia at a predetermined future time according to the following algorithms:
(a) if the glucose level is ≥150 mg/dL, then the glucose sensor continues to collect glucose data; or
(b) if the glucose level is <150 mg/dL, then the ROC of the glucose level is determined,
  (i) if the ROC is between −0.5 mg/dL/min and −5 mg/dL/min, then a time to a low glucose level ($t_{low}$) is determined based on the ROC,
    (A) if the $t_{low}$ is <30 minutes, then the patient's glucose level is predicted to be low and the module generates an alert, takes a blood sample, and sends a command to inject glucagon; or
    (B) if the $t_{low}$ is not <30 minutes, then the glucose sensor continues to collect glucose data; or
  (ii) if the ROC is not between −0.5 mg/dL/min and −5 mg/dL/min, then the glucose sensor continues to collect glucose data.

* * * * *